United States Patent
Eberl et al.

(10) Patent No.: US 6,916,096 B2
(45) Date of Patent: Jul. 12, 2005

(54) SYSTEM AND METHOD FOR RECORDING THE RETINAL REFLEX IMAGE

(76) Inventors: Heinrich A. Eberl, Hochvogelweg 3, 87463 Probstried (DE); Roland H. C. Eberl, Perhamerstr. 76, 80687 Munich (DE); Hans Brandl, Hochfellnstrasse 7, 83093 Bad Endorf (DE)

( * ) Notice: Subject to any disclaimer, the term of this patent is extended or adjusted under 35 U.S.C. 154(b) by 190 days.

(21) Appl. No.: 09/962,005

(22) Filed: Sep. 22, 2001

(65) Prior Publication Data

US 2002/0036750 A1 Mar. 28, 2002

(30) Foreign Application Priority Data

Sep. 23, 2000 (DE) .......................................... 100 47 237

(51) Int. Cl.[7] .............................. A61B 3/00; A61B 3/14
(52) U.S. Cl. ..................................... 351/209; 351/246
(58) Field of Search ................................ 351/205, 208, 351/209, 210, 221, 222, 223, 224, 226, 239, 246, 237, 243; 345/7, 8; 600/558

(56) References Cited

U.S. PATENT DOCUMENTS

| | | | |
|---|---|---|---|
| 4,213,678 A | | 7/1980 | Pomerantzeff et al. .......... 351/7 |
| 4,758,080 A | | 7/1988 | Howland .................... 351/211 |
| 4,886,351 A | | 12/1989 | Sabban et al. ............... 351/221 |
| 5,106,179 A | | 4/1992 | Kamaya et al. ............. 351/158 |
| 5,177,511 A | * | 1/1993 | Feuerstein et al. .......... 351/205 |
| 5,202,711 A | * | 4/1993 | Klingbeil .................... 351/224 |
| 5,467,104 A | | 11/1995 | Furness, III et al. ............. 345/8 |
| 5,506,633 A | * | 4/1996 | Sperling .................... 351/206 |
| 5,550,602 A | * | 8/1996 | Braeuning .................. 351/243 |
| 5,644,642 A | | 7/1997 | Kirschbaum ................ 382/103 |
| 5,703,637 A | * | 12/1997 | Miyazaki et al. ............. 348/53 |
| 5,914,770 A | | 6/1999 | Bergner et al. ............. 351/206 |
| 6,027,216 A | * | 2/2000 | Guyton et al. .............. 351/200 |
| 6,045,515 A | * | 4/2000 | Lawton ...................... 600/558 |
| 6,149,272 A | | 11/2000 | Bergner et al. ............. 351/221 |
| 6,213,627 B1 | | 4/2001 | Abersfelder et al. ........ 362/487 |
| 6,227,667 B1 | | 5/2001 | Halldorsson et al. ....... 351/260 |
| 6,386,706 B1 | | 5/2002 | McClure et al. ............ 351/237 |

FOREIGN PATENT DOCUMENTS

| | | |
|---|---|---|
| DE | 3614153 A1 | 1/1987 |
| DE | 3607 721 A1 | 9/1987 |
| DE | 196 31 414 A1 | 2/1998 |
| DE | 197 28 890 A1 | 2/1999 |
| EP | 511 154 A2 | 10/1992 |
| EP | 562 742 A1 | 9/1993 |
| EP | 473 343 B1 | 11/1995 |
| EP | 0 722 108 A1 | 7/1996 |
| WO | WO 88/03396 | 5/1988 |
| WO | WO 90/09142 | 8/1990 |
| WO | WO 00/72745 A1 | 7/2000 |

OTHER PUBLICATIONS

Webb, Robert H. et al., *Confocal Scanning Laser Ophthalmoscope*; Applied Optics, vol. 26, No. 8, Apr. 15, 1987.

Cambell, F.W. et al., *Optical and Retinal Factors Affecting Visual Resolution*; J. Physiol. (1965), 181, pp. 576–593.

(Continued)

*Primary Examiner*—Brian L. Casler
*Assistant Examiner*—John R. Sanders
(74) *Attorney, Agent, or Firm*—Ivan David Zitkovsky

(57) ABSTRACT

A system and method for eye examination by scanning light scattered from an area of the retina and projecting light into the eye includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed to analyse a patient's sight.

12 Claims, 12 Drawing Sheets

OTHER PUBLICATIONS

Delori, Francis C. et al., *Spectral Reflectance of the Human Ocular Fundus*; Applied Optics, vol. 28, No. 6, Mar. 15, 1989.

Webb, R.H. et al., *Flying Spot TV Ophthalmoscope*; Applied Optics/vol. 19, No. 17, Sep. 1, 1980, pp. 2991–2997.

Wilson, Bruce A. et al., *A Flying–Spot Laser Scanner for Tracking Eye Movements*; Proceedings 18th Annual International Conference of IEEE Engineering in Medicine and Biology Society, Oct. 31–Nov. 3, 1996, Amsterdam.

Irie, Kenji, et al., *A Laser–Based Eye–Tracker System: Improvements in Reliability of Operation*; Proceedings Annual Conference of ACPSEM (NZ Branch), Nov. 26–27, 1998, Christchurch, 14.

Brandl, H. et al., *Eagles: Electronically Active Glasses by Laser Enhancement System*; 97th DOG Annual Meeting 1999; Abstract http://www.dog.org/1999/e–abstract99/136.ntml.

Virree, E., et al. The Virtual Retinal Display: A New Technology for Virtual Reality and Augmented Vision in Medicine, *In Proceedings of Medicine Meets Virtual Reality*, San Diego, CA, pp. 252–257, (1998) Amsterdam: IOS Press and Ohnsha.

\* cited by examiner

CONCENTRIC
CIRCULAR SCAN

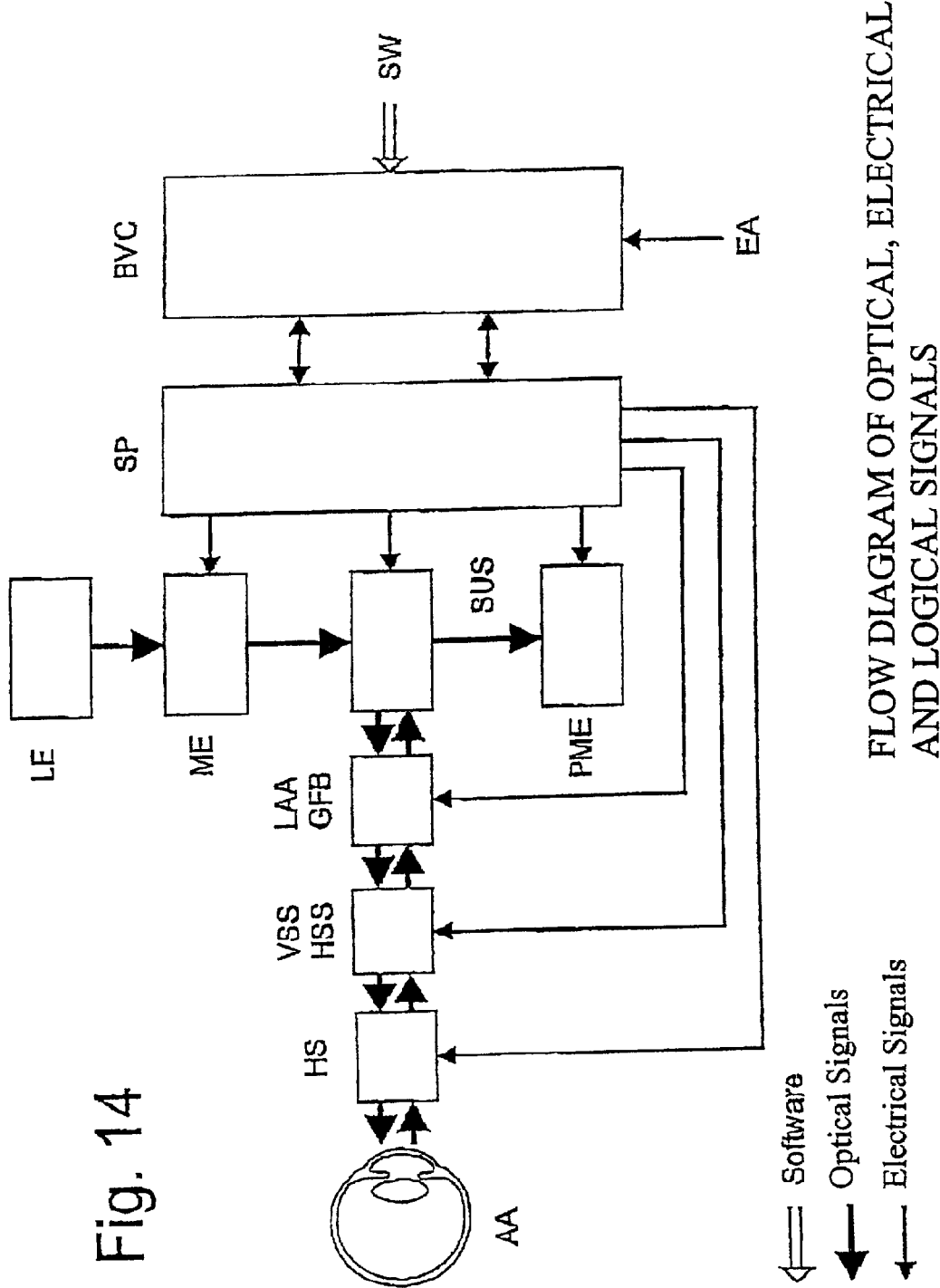

SYSTEM AND METHOD FOR RECORDING THE RETINAL REFLEX IMAGE

FIELD OF THE INVENTION

The invention relates to a system and method for eye examination by scanning light scattered from an area of the retina and projecting light into the eye.

BACKGROUND

Optical devices are known from the German laid open patent applications DE OS 196 31 414 A1 and DE 197 28 890, which make it possible to capture the retina reflex image and to superimpose additional images in the eye.

Since the devices and systems described in the above-mentioned applications are preferably designed in the form of a pair of spectacles, they will for the sake of simplicity also be referred to in the following as a spectacle system. This term does not imply any restriction, and other embodiments of such devices and systems, instead of the "spectacle system" can be used in the contexts described below.

There is a need for novel methods and systems enabling examination of the eye or improving vision, and such systems and methods may be improvements of the embodiments described in the DE 196 31 414 A1 application.

SUMMARY OF THE INVENTION

The present system and methods are particularly useful for examination of the eye and for medical engineering and/or ophthalmology, especially in precision surgery and in the field of strabology, i.e., in studying the eye muscles and the function of the eye linked to the muscles, and also in the field of neuro-ophthalmology.

According to one aspect of the invention, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed to analyse a patient's sight.

Preferably, this aspect includes one or more of the following features: The receiver unit is constructed to generate a captured image based on said captured light. The projection unit generate said light configuration forming a projection image. The projection image is delivered onto the retina. The scanner includes a beam deflection unit.

Alternatively, the projection unit is constructed to generate a predetermined distribution of patterns on the retina. The projection unit is constructed to generate a predetermined distribution of patterns over several selected regions of the retina.

The scanner, the receiver unit and the projection unit are designed to further analyse a movement of a patient's eye by generating random dot patterns on the retina of the eye. The scanner, the receiver unit and the projection unit are designed to analyse a patient's eye by generating random dot patterns on the retina of the eye. The scanner, the receiver unit and the projection unit are designed to analyse the spatial vision of a patient's eye by generating random dot patterns on the retina of the eye.

The scanner includes a beam splitter constructed and arranged to transmit into the eye outside light and to reflect scattered light from the retina of the eye to the receiver unit. The beam splitter is constructed and arranged to transmit into the eye light of the light configuration generated by the projection unit. The receiver unit includes an optoelectronic detector. The projection unit includes a laser source.

The system includes a scanning capture device for capturing an image of an outside object projected onto the retina. The system includes a pair of spectacles with lenses associated with the scanner. The lenses may include inner surfaces providing concave mapping beam splitter mirrors.

The scanner, the receiver unit and the projection unit are arranged to synchronise in time and space scanned and projected images. The scanner, the receiver unit and the projection unit are arranged for dynamically adjusting the scanning time for desired resolution, detection time, and illumination time. The scanner, the receiver unit and the projection unit are arranged for dynamically adjusting a size of the scanning spot. The scanner, the receiver unit and the projection unit are arranged for dynamically adjusting the pitch of scanning tracks. The scanner, the receiver unit and the projection unit are arranged for dynamically adjusting a size of the area.

The receiver unit is constructed to determine the absolute brightness of the eye surrounding based on the captured light. The receiver unit is constructed to determine the absolute colour temperature of the light based on the captured light.

The scanner includes a two-axis scanning device for capturing parallel focussed beams scattered back from a point on the retina and emerging from the eye. The two-axis scanning device is constructed to map and deflect the parallel focussed beams. The two-axis scanning device is constructed to direct the parallel focussed light to an optoelectronic detector of the receiver unit in order to affect a serial capture of the retina reflex. The two-axis scanning device is constructed to map on the retina a light beam from the projection unit in the opposite direction to the capturing the parallel focussed beams via the same light path.

The system includes a beam switch constructed and arranged to switch light paths between scanning the retina by the receiver unit and projection onto the retina by the projection unit.

The system includes a pair of spectacles with at least one lens having an inner concave surface being arranged to have an optical scanning axis, when considered from the scanner, running into a light-absorbing radiation sink. The scanner may include a concave auxiliary mirror, a convex auxiliary mirror, or both.

The scanner, the receiver unit and the projection unit are arranged for separate image scanning and projection over time alternating at a fixed image frequency. The scanner, the receiver unit and the projection unit are arranged in a way that image scanning can be interrupted to perform image projection into the eye. The scanner and the receiver unit are arranged to perform image scanning over the area of the retina in accordance with a known video standard. The scanner and the receiver unit are arranged to perform image scanning over the area of the retina in a raster-like pattern. The scanner and the receiver unit are arranged to perform image scanning over the area of the retina in a spiral pattern.

The receiver unit may include a plurality of beam splitters and photodetectors arranged to detect independently signals of a plurality of spectral ranges. The projection unit may include a plurality of light sources and beam splitters for delivering emitted light to the eye over a single illumination channel.

The scanner, the receiver unit and the projection unit are arranged to be coupled by a rigid beam guide or by a flexible beam guide. The projection unit may include lasers, image modulators and beam splitters optically coupled via an optical fiber to the scanner. The receiver unit may include photoreceivers and beam splitter optically coupled via an optical fiber to the scanner.

The system may include a beam-focussing device integrated into a beam path for varying a size of the image spot on the retina. The system may include a variable field diaphragm integrated into the beam path for varying a size of a scanning spot on the retina. The system may include an optical switch for at least partially cutting off external light.

The system includes an image-processing computer for processing images captured in synchronisation with image scanning of the retina. The image processing computer, the receiver unit and the projection unit are arranged to use at least one electro-optical modulator to creating an image on the retina synchronously with the scanning of the retina. The image processing computer, the receiver unit and the projection unit are arranged to synchronize in time and space an image projected onto the retina with an image scanned over the area. The image-processing computer is constructed to synchronize computer-generated information and the scanned image, and the projection unit is arranged to project the information on the retina.

The system may includes an image processing computer for processing images, wherein the image processing computer, the receiver unit, and the projection unit are arranged to capture scanned images during image projection and to deliver to the captured images to the image processing computer while at least partially cutting off external light.

The scanner is constructed and arranged to reverse a beam path by 180° compared to a direction of the projection for illuminating an object seen by the eye with a laser image derived by a computer.

The scanner and the receiver unit are arranged to perform circular image scanning over the area of the retina. The scanner and the receiver unit are arranged to perform elliptical image scanning over the area of the retina and to perform circular scanning by merging focal points of the elliptical scanning.

The scanner and the receiver unit are arranged to perform elliptical image scanning over the area of the retina. The scanner and the receiver unit are arranged to perform elliptical image scanning over the area of the retina and employ the elliptical scanning to center the scanner without any other external sensors by determining outside edges of the pupil. The scanner and the receiver unit are arranged to perform elliptical image scanning over the area of the retina by scanning from the outside inwards. The scanner and the receiver unit are arranged to perform elliptical image scanning over the area of the retina by scanning from the inside outwards.

The system may include an image processing system for adjusting brightness of an image captured by the receiver unit.

The receiver unit and the projection unit are arranged to process a captured image and transform a wavelength for projecting the image on a different wavelength.

The receiver unit and the projection unit are arranged to evaluate a captured image at a wavelength or wavelength range outside of the range of perception of the eye and then transform into a visible wavelength or visible range.

The receiver unit and the projection unit are arranged to transform black-and-white information into color information. The receiver unit and the projection unit are arranged to evaluate black-and-white vision (rod vision). The receiver unit and the projection unit are arranged to evaluate colour vision (cone vision).

The system may include a processor programmed to perform a suitable algorithm (e.g., a Fourier transformation) for compensating sight defects of the eye. The system may include an external sensor cooperatively arranged with the scanner for determining the position of the pupil.

The receiver unit is arranged to evaluate a captured image with regard to the image content in order activate external reactions and control functions. The receiver unit may be arranged to compare the image content of the left and right eye.

This aspect of the invention may include one or more of the following features: The system is arranged to compare the position of the pupils. The system is arranged to compare the image contents of the fovea centralis of both eyes. The system is arranged to use the position of the pupils and the image contents of the fovea centralis of both eyes to determine the visual axis for triangulation (determining distances). The system is arranged to use the image information of the eye for determining the absolute brightness of the surroundings. The system is arranged to use the image information of the eye for determining the absolute color temperature of the light.

The receiver unit and the projection unit are arranged to determine the size of the pupil. The system may include an image processing system arranged to adjust brightness of a captured image to shift the physiological apparent sensitivity a less sensitive range.

According to another aspect, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed to determine anomalies in the motor response of the eyeball.

This aspect includes one or more of the following features: The scanner, the receiver unit and the projection unit are cooperatively designed to determine anomalies in the motor response of the eyeball by monitoring a position of the eyeball. The receiver unit and the projection unit are cooperatively designed to determine anomalies in the motor response of the eyeball by monitoring orientation of the eyeball. The receiver unit and the projection unit are cooperatively designed to determine the squint angle by determining and monitoring the center point of both eyes. The receiver unit and the projection unit are cooperatively designed to determine the squint angle by determining and monitoring the center point of both eyes.

The receiver unit and the projection unit are cooperatively designed to detect parasympathetic/sympathetic efferences, by monitoring and evaluating the motor response of the pupil. The receiver unit and the projection unit are cooperatively designed as a synoptophor. The receiver unit and the projection unit are cooperatively designed as a synoptometer with no device convergence. The receiver unit and the projection unit are cooperatively designed as a device for determining cyclodeviation. The receiver unit and the projection unit are cooperatively designed as a phase difference haploscope. The receiver unit and the projection unit are cooperatively designed as a device for detecting phoria identical to the visual axis with different lines of sight.

According to another aspect, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed to check the function of the retina by making use of a sample electro-retinogram (ERG) and a correlation device, with which an image played onto the retina can be brought into correlation with the ERG actually determined.

According to yet another aspect, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed to measure the contrast sensitivity of a patient's sight.

Preferably, the scanner, the receiver unit and the projection unit are cooperatively designed to measure the contrast sensitivity of a patient's sight as a function of the spatial frequency.

According to yet another aspect, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed for white-noise-field campimetry.

According to yet another aspect, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed to determine the extent and the position of central field of vision defects (scotomae).

According to yet another aspect, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed as a visual enabling for precision surgery device (VEP).

According to yet another aspect, a system for eye examination includes a scanner, a receiver unit, and a projection unit. The scanner is constructed and arranged to scan an area on the retina. The receiver unit is optically coupled to the scanner and constructed and arranged to capture light scattered back from the area of the retina. The projection unit is constructed to generate and optically couple a light configuration to the scanner for delivering the light configuration into the eye relative to the area of the retina, wherein the scanner, the receiver unit and the projection unit are cooperatively designed to perform as a scanning laser ophthalmoscope device (SLO).

According to yet another aspect, a system for capturing the retina reflex image by means of a scanning system for scanning an image on the retina and for delivering additional optical signals into the eye, in which a beam splitter is used to transmit beams from the outside world into the eye and to reflect the beams scattered back by the retina of the eye, a receiver unit is used to capture the beams scattered back, and a projection unit is used to project light beams into the eye, in order to generate a copy on the retina, which is superimposed on the image originally mapped on the retina. The scanning system, while scanning, deflects the beams coming from the retina and transmits them to an opto-electronic detector for the serial capture of the retina reflex. The system is used and/or designed to analyse a patient's sight, by using the projection unit to generate a predetermined pattern or a predetermined distribution of patterns on the retina or on selected regions of the retina.

Preferably, the system is used and/or designed to analyse the movement patterns and/or the noise fields and/or the spatial vision of a patient's eye, by generating random dot patterns on the retina by means of the projection unit, for test purposes.

According to yet another aspect, a method of eye examination, comprising the acts of scanning an area on the retina; capturing light scattered back from the area of the retina; generating a light configuration and delivering the light configuration into the eye relative to the area of the retina; and analysing a patient's sight based on the captured light and the generated light configuration.

According to yet another aspect, a method of eye examination, comprising the acts of scanning an area on the retina; capturing light scattered back from the area of the retina; generating a light configuration and delivering the light configuration into the eye relative to the area of the retina; and determining anomalies in the motor response of the eyeball.

The determination of anomalies in the motor response of the eyeball may be performed by monitoring a position of the eyeball or by monitoring orientation of the eyeball or both.

The method may include determining the squint angle by determining and monitoring the center point of both eyes.

The method may include detecting parasympathetic/sympathetic efferences by monitoring and evaluating the motor response of the pupil.

According to yet another aspect, a method of eye examination, comprising the acts of scanning an area on the retina; capturing light scattered back from the area of the retina; generating a light configuration and delivering the light configuration into the eye relative to the area of the retina; and checking the function of the retina by making use of a sample electro-retinogram (ERG) and a correlation device, with which an image played onto the retina can be brought into correlation with the ERG actually determined.

According to yet another aspect, a method of eye examination, comprising the acts of scanning an area on the retina; capturing light scattered back from the area of the retina; generating a light configuration and delivering the light configuration into the eye relative to the area of the retina; and measuring the contrast sensitivity of a patient's sight.

The measuring the contrast sensitivity of a patient's sight may be performed as a function of the spatial frequency.

According to yet another aspect, a method of eye examination, comprising the acts of scanning an area on the retina; capturing light scattered back from the area of the retina; generating a light configuration and delivering the light configuration into the eye relative to the area of the retina; and performing white-noise-field campimetry.

According to yet another aspect, a method of eye examination, comprising the acts of: scanning an area on the retina; capturing light scattered back from the area of the retina; generating a light configuration and delivering the light configuration into the eye relative to the area of the retina; and determining the extent and the position of central field of vision defects (scotomae).

According to yet another aspect, a method of eye examination, comprising the acts of scanning an area on the retina; capturing light scattered back from the area of the retina; generating a light configuration and delivering the light configuration into the eye relative to the area of the retina; and performing visual enabling for precision surgery (VEP).

Various physiological and pathophysiological conditions of the eye and the related nervous system (including optic nerve) are described in "Clinical Ophtalmology: A Systemic Approach" by Jack J. Kanski (published by Butterworth-Heinemann); "The Retina" by Stephen J. Ryan (published by Mosby-YearBook); and "Atlas of Clinical Opthalmology" ed. by Roger A. Hitchings et al. (published by Gower-Mosb) all of which are incorporated by reference for all purposes.

The problem of the low degree of mapping (reflection) of the retina, which is dependent on the wavelength, can be countered by means of appropriate capture sensors, such as those with a sensitivity ranging between 0.2 mlx and 1 mlx, it being preferable for wavelength-dependent reproduction characteristics to be used.

In particular the scanning process described in the laid open patent applications DE OS 196 31 414 A1 and DE OS 197 28 890, preferably spiral scanning identical to the visual axis, makes it possible to return exactly to a specific locus on the retina and to track the line of sight precisely, taking the irregular, interrupted movements into account.

The system for capturing the retina reflex image by means of a scanning system for scanning an image on the retina and for delivering additional optical signals into the eye can be converted, by means of simple additional modules, such as those including an appropriate means of delivering reference information to the unit for analysing the signals received, into devices which have been used in the past as special equipment in medical engineering or ophthalmology.

The principal applications in medical engineering are in the fields of ophthalmic surgery, VEP (visual enabling for precision surgery), laser ophthalmology in uses corresponding to an SLO (scanning laser ophthalmoloscope), contrast sensitivity measurement as a function of spatial frequency or noise field ampimetry. Using white-noise-field campimetry based on work conducted by Prof. Aulhorn (a white-noise-field corresponds, for example, to steady noise on a television screen), it is possible at an early stage, under experimental conditions, to detect and describe field of vision deficiencies with a sensitivity of greater than 80%.

In the field of strabology and neuro-ophthalmology, the following functions can be represented with the system: The function of a co-ordimetrical device corresponding to the Hess screen. The function of a device for registering phoria identical to the visual axis with different lines of sight. The function of a synoptophor/synoptometer with no device convergence. The function of a haploscope, especially a phase difference haploscope, i.e. a device for determining the relative width of convergence and fusion in binocular vision. The function of a device for determining cyclodeviation, i.e. the rotation of the eyeball about the visual axis. The function of a device for examining defects in the rest position, such as angular sight defects, phoria (imbalance of the muscles in the pair of eyes), tropia and strabismus. The function of a device for checking the function of the retina and analysing movement patterns, noise fields or an eye's spatial vision. The function of a device for determining the squint angle and the pupil motor response.

BRIEF DESCRIPTION OF THE DRAWINGS

FIG. 14 shows the flow of optical, electrical and software signals.

DETAILED DESCRIPTION OF PREFERRED EMBODIMENTS AND EXAMPLES

The present systems and methods are arranged for examination of the eye or the eyesight. The devices make it possible to capture in backscattering the image of the outside world projected onto the retina of the human eye, to modify that image with electronic image processing, or, where appropriate, to supplement it with additional information, and to superimpose it on the original image using laser beam modulation and deflection back into the eye.

Figure 2:
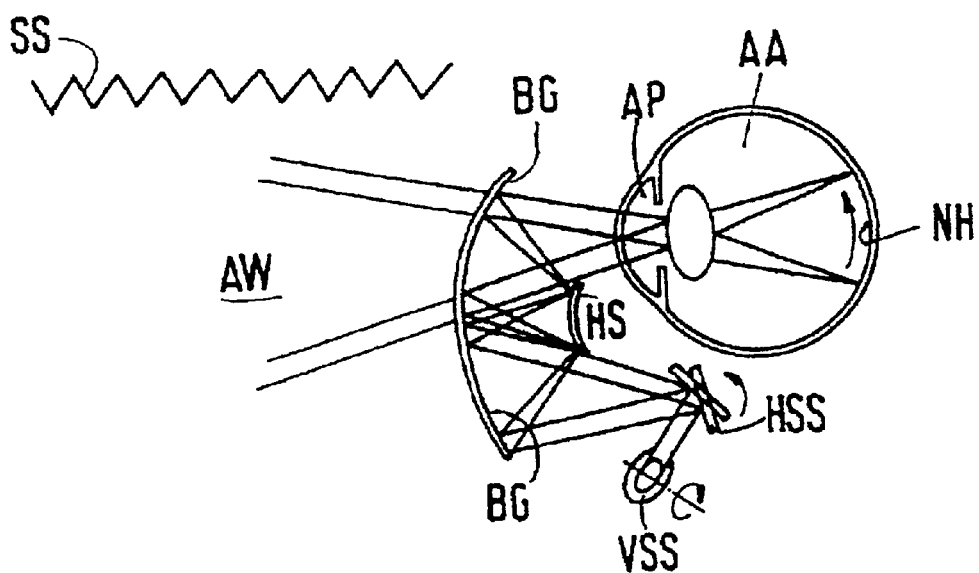
FIG. 2 is a schematic depiction of an embodiment of the device for capture and projection into the eye, wherein the mapping is effected between the scanner and the eye at the concave auxiliary mirror surface BG min, a convex auxiliary mirror HS min and the concave inner surface of the spectacle lens BG.
Figure 3:
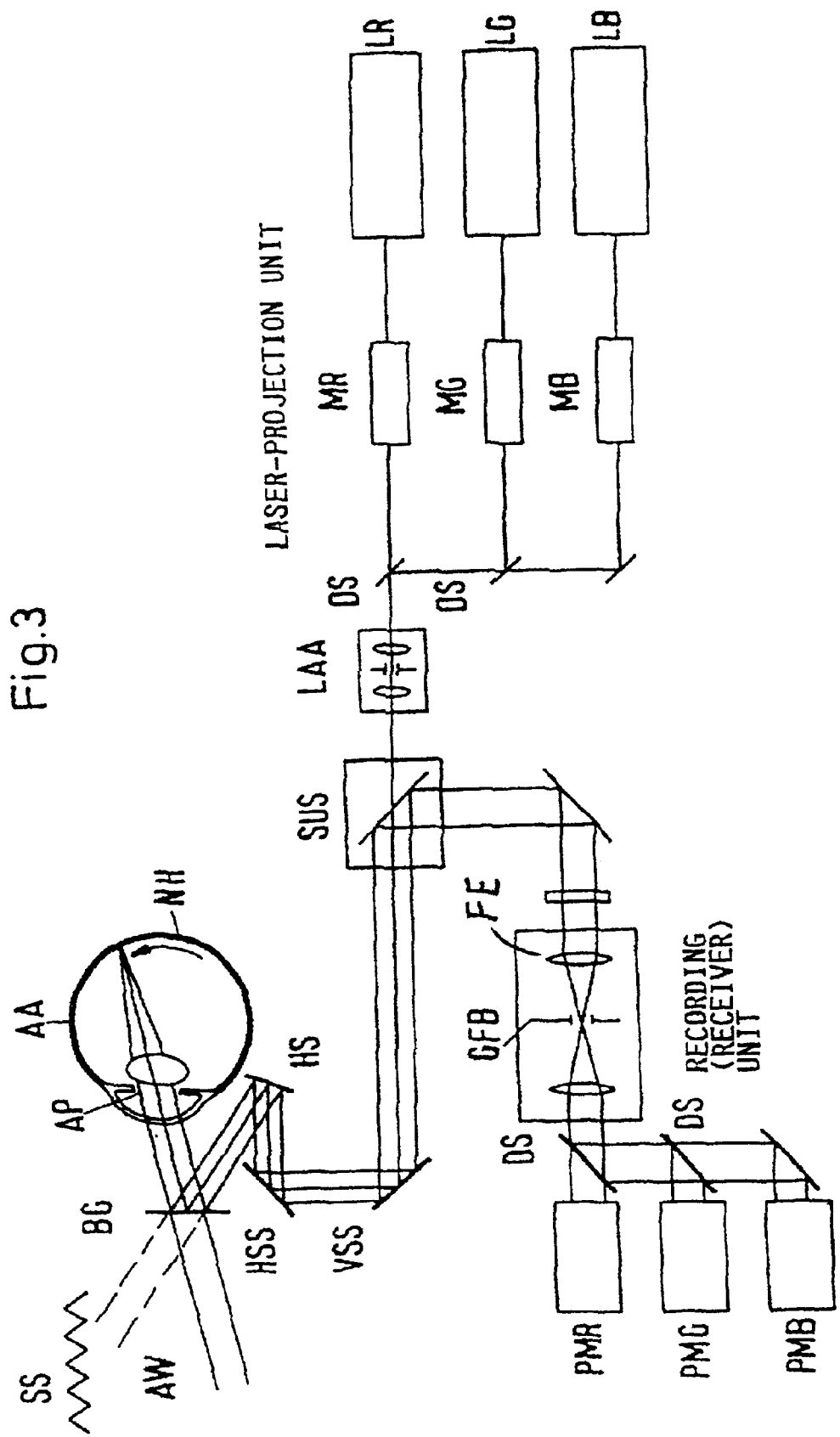
FIG. 3 is a schematic depiction of an embodiment of the rigid beam path between the device for capture and projection including photoreceivers and laser modulators.
Figure 4:
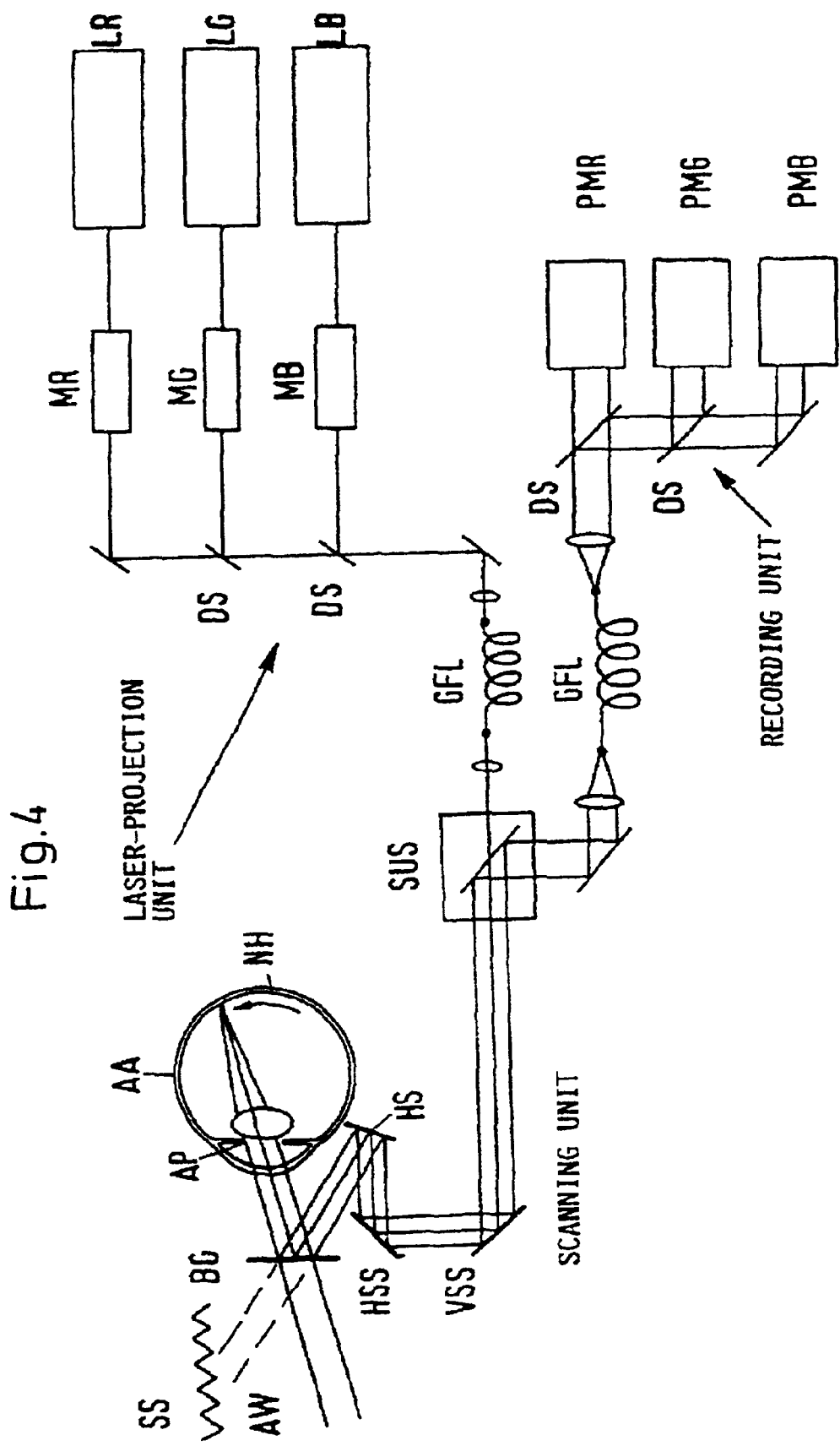
FIG. 4 is a schematic depiction of an embodiment of the flexible coupling of the device for capture and projection to the beam switch and scanning unit including flexible glass fibers.

Referring to FIGS. 3 and 4, a device for recording an image reflected from the retina and projecting a modified image onto the retina includes a scanner system, a receiver unit and a projection unit. The scanner system (for example, shown in FIGS. 1 and 2) includes a deflection unit with a set of mirrors and scanning devices such as mirrors BG and HS, a horizontal scanner HSS, and a vertical scanner VSS. The recording (receiver) unit includes a visual field aperture GFB, several of mirrors DS and several separate detectors PMR, PMG and PMB. The projection unit includes several separate modulators MR, MG, MB optically coupled to the respective laser sources LR, LG, and LB. The receiver unit and the projection unit may provide data to and receive data from a computer or an image processing system. Based on the images acquired by the receiver or images provided by the projection unit, the computer can evaluate a patient's eyesight, or can evaluate a physiological or patophysiological condition of the examined eye. The computer can compare date acquired from the right eye and the left eye, or can compare the measured data to a statistical data corresponding to normal eyesight or a known physiological or patophysiological condition.

The systems shown in FIGS. 3 and 4 utilize a rapid progress in the fields of image scanning capturing and processing which are further improved by the constant increase in the speed of image processing by computers. In general, electronic image processing can manipulate images that have been recorded by cameras, scanning systems and sensors, both in the visible light range and in ranges of the electromagnetic spectrum, such as the infrared, radio and X-ray ranges. After being processed electronically, the images are reproduced as individual images or as moving images on an image display surface (display) for capturing the information from the eye.

With the help of electronic image processing, it is first of all possible to make particular elements contained in the image more easily recognisable. Techniques introduced for this purpose include, for example, spatial frequency filtering, edge enhancement, image data compression, image correlation, dynamic response reduction and false colour coding. Apart from this, other techniques are concerned with the superimposition or subtraction of additional images from various spectral ranges, or the superimposition of stored plans, maps and drawings onto the original image.

For many applications, an effectively distortion-free graphical representation is of great benefit for the eye, such as, for example, when piloting an aircraft, steering a ship or vehicle, or controlling and monitoring processes and production lines. With image processing, it is possible to increase or reduce the information content of the current direct image in a targeted manner. The applications range from enhancing the image contrast to inserting additional information and highlighting details and hazards.

In most of these applications, it is a disadvantage that the electronic camera amounts to a "second ocular system" separate from the human eye, because, first of all, the images are seen from a different capture location and, secondly, they are displayed on the screen in a different observation location from the eye. The human eye thus has to shift constantly between direct and indirect observation, with different angles of view, image details and size ratios, which leads to physical impairments and delays in decision-making processes.

These restrictions have been partially solved by means of the technique of "head-up display (HUD)" in the case of piloting fighter aircraft, in that important information, such as instrument displays and targets are projected into the open goggles of the pilot's helmet and thus into the pilot's field of vision. This technique is also being employed on an experimental basis in the car industry to project instrument displays into the windscreen, so that the driver is not distracted from observing the road ahead of him.

A known further development of this technique is "virtual reality", or "cyberspace". In this case, HUD is used in closed spectacles, i.e. spectacles in which the wearer's view of his surroundings is blocked off, to project complete moving spatial images into the eye in a realistic way such that they change interactively in accordance with body movements, such as locomotion, arm movements, finger movements, or head and eye movements.

In HUD, the image is generated on a screen and projected into the eye after being reflected on the surface of the spectacles. The eye in effect sees through the spectacles, which act as complete mirrors, and looks "round corners" to see the display, and, in the case of open spectacles with a semi-reflecting mirror, sees the outside world at the same time. Since the display is fixed to the head, the image follows the head movements.

Some HUDs are equipped with an "eye tracker", which tracks the movements of the eye using a movement sensor on the eyeball or using a camera which tracks the movements of the pupils or traces the structure of the blood vessels in the retina. The image projected in the HUD can then be shifted electronically in accordance with the movements within the field of vision.

In order to relax the eye without accommodation, the image of the HUD can be displaced to "infinity" via the projection optics. By adjusting different angles of sight for the two eyes towards the same object, stereoscopic, i.e. spatial vision becomes possible.

These applications and techniques make clear first of all the high state of development in electronic image processing, which is already capable, with an acceptable level of technical effort, of processing moving images in a reasonable quality and almost without distortion, and secondly the growing demand for the direct transmission of images into the eye.

In prior art systems, the accuracy of the system of automatically tracking eye movements with the "eye tracker" is considerably poorer than the accuracy of alignment and image resolution of the eye. As a consequence of this, the image inserted into the field of vision hovers or dances around, which leads to inaccuracy in finding the target and tires the eye.

For this reason, the existing applications for displaying complete images have been restricted to closed spectacles, i.e. inserting exclusively extraneous images. On the other hand, the applications of open spectacles with a view of the outside world in addition are still restricted to inserting simple additional information in the form of text, symbols or image outlines.

The complete overlapping, in time and space, of inserted images onto the real image perceived by the eye presupposes that the two images on the retina also correlate exactly in time an space. This can only be achieved by capturing the retina image directly and subsequently projecting the new image onto the real image congruently and almost without any delay, which is the object of the invention.

At this point, we shall first of all describe and discuss the state of the art of capturing retina reflex images, scanning images from the interior of the eye and projecting laser images directly into eye, since the invention proceeds from this prior art. The technical implementation of continuously mapping the retina reflex of the outside world presupposes an acceptable optical reflection of the retina. Its reflection capacity, for example, has been measured in detail by F. C. Delori and K. P. Pflibsen in the article entitled "Spectral reflectance of the human ocular fundus", Applied Optics, Vol. 28, No. 6, (1989). From the blue visible range (450 nm) with the lowest value of 0.2%, the reflectance of the fovea centralis in the retina increases monotonously to 10% in the long-wave red range (750 nm). In the range where the eye is most sensitive and vision is most acute, namely in the green-yellow range between 500 nm and 600 nm, the reflectance is then between 1% and 2%.

A system for capturing this reflex must therefore be designed for a luminance of the retina which is lower by a factor of 50–100 relative to that of the region in which the object is located. A further impairment of the available quantity of light results from the size of the pupil, which is 1–7 mm in diameter, and which is relatively small compared to conventional technical capture systems, such as cameras and video cameras. For these two reasons, if the light reflected by the retina is to be captured, a particularly sensitive light sensor will be required.

It is known that a structured reflex image is formed on the retina in the region the fovea centralis when an object is mapped in the eye. This is described, for example, by Campell, F. W. and Green, D. G. in the article: "Optical and Retinal Factors Affecting Visual Resolution", J. Physiol. 181, 576–593 (1965). In this case, a brightly illuminated extended grid structure was mapped on the retina, and the image reflected by the eye was deflected out of the beam path with a splitter mirror and mapped in focus outside the eye in one focal plane. The two-dimensional mapping of the grid after its reflection on the retina, i.e. after it had passed through the eye twice, served to determine the modulation transfer function of the eye. The photometric evaluation showed that the quality of the reflex image comes very close to the quality of the image perceived by the eye itself.

The closed static capture device used by Campell et al., with extremely bright image illumination (flash light) and with the eye immobilised, is not suitable for capturing the low-light dynamic images of the outside world on the retina during the rapid, natural spontaneous movements of the eye. This requires light-sensitive, rapid detectors and a capture technique which very efficiently suppresses parasitic light in the open beam path and can capture images at least at the refresh rate of conventional video standards.

There are also CCD cameras which capture all the pixels in parallel after a fixed integration time. There are also serially scanning image capture systems with individual detectors (photodiodes or photomultipliers), in which the pixels are scanned one after the other in time. Both techniques are adapted to the conventional video standards. One fundamental advantage of using the CCD capture method is the long integration time in each pixel of, for example, 20 ms, compared to the short dwell time in each pixel of only 40 ns in the case of scanning. The serial capture method does, however, have a number of other advantages over the parallel capture method when it comes to capturing the very weak, rapidly changing light signals against an extremely noisy background, and these advantages make up for the disadvantage of the short integration time. These are:

Serial signal processing, which makes direct analogue further processing of the image possible in real time, efficient suppression of scattered light by visual field of the scan at any particular moment, low-noise, high pre-amplification of the avalanche photoiodes and photomultipliers used, high signal dynamics, which are useful in view of the major variations in brightness of the image on the retina, efficient analogue noise suppression, for example by phase lock-in detection or signal correlation and simple correction of mapping errors.

An advantage of serial image scanning is that it opens up the additional possibility of combining it with time-lag synchronous serial laser image projection into the eye.

In view of these benefits offered by serial capturing compared to film and video recording, the method has been used especially for image capturing in microscopes since the early fifties. Serial scanning can achieve three things: firstly, two-dimensional illumination of the object and pin-point scanning with a photo-electric receiver; secondly, scanning the object with a pin-point light source and two-dimensional capturing with the photo-electric receiver; and thirdly, pin-point illumination and simultaneous pin-point scanning with the photo-electric receiver, using the same scanning direction. The first two methods are referred to as "flying spot" and the third as "confocal scanning" capture techniques.

In the first two cases, either the source or the receiver is fixed, while the receiver or the source is in motion on the object. In the third, the source and the receiver are mapped together on the scanning spot (confocally), but they are immobile relative to one another.

In this sense, capturing the two-dimensional retina reflex of the outside world with a scanning photo-electric receiver, as proposed by the invention, is the first type of "flying spot" image capture technique. Since the source of illumination and the photo-electric receiver are mapped together in a pin-point on the retina while scanning, time-lag synchronous laser image projection using the same scanning device can be understood as a confocal scanning technique, but not as a confocally scanning capture technique, because the roles of the photo-electric receiver and the laser have been reversed compared to the conventional application. In the invention, the signals received are used to modulate the laser source with a time lag, whereas in the standard method, the laser source is used to illuminate while receiving the light signals at the same time.

The present systems also utilize advantages described in the following publications.

O. Pomerntzeff and R. H. Webb were the first to describe the second type of "flying spot" capture technique using a scanned laser beam as the source of illumination and a rigid large-format photomultiplier receiver to capture the internal structure of the eye in the U.S. Pat. No. 4,213,678 from September 1980 "Scanning Ophthalmoscope for Examining the Fundus of the Eye".

An extension of this technique to a confocal arrangement with simultaneous scanning of the laser beam and the receiving axis of the photomultiplier was disclosed by R. H. Webb, G. W. Hughes and F. C. Delori in the article "Confocal scanning laser ophthalmoscope" in Applied Optics, Vol. 26, No. 8, pp. 1492–1499 (1987).

In this device, the retina is scanned in a grid pattern by a laser beam. The laser beam illuminates the original point by point and line by line. The photo-electric receiver (photomultiplier) measures the light reflected in each case and converts the sequence of measured values into a video signal. Finally, a television monitor displays the video signal as an image. These three processes take place in exact synchronisation. While the laser beam scans the background of the eye line by line, the television signal is assembled at the same time.

The laser beam first of all passes through a modulator, by which it is possible to control the illumination intensity. Horizontal line deflection is usually carried out with a rapidly rotating polygonal mirror, while vertical deflection is effected by an oscillating mirror. The center of rotation of the scanning movement is located in the plane of the pupil. The light reflected or scattered back from the fundus of the eye is collected over the entire aperture of the pupil and delivered to the photo-electric receiver via a mapping optical system. The beam deflection is neutralised as a result, and one obtains a stationary pencil of light rays, which is mapped on a small detector surface.

Direct projection of modulated light stimuli and patterns has been used in modern laser scanning ophthalmoscopes (such as those made by the Rodenstock company in Munich, for example) mainly for analysing sight, video vision determination and measurements of contrast sensitivity on only one laser wavelength at a time.

Other proposals regarding the direct transmission of images into the eye with lasers are known from the following two documents: the European Patent 0 473 343 B1 of November 1995 to Sony Corporation entitled "Direct viewing picture image display apparatus" discloses a direct viewing picture display apparatus, which substantially comprises only the technical solutions known from the earlier publications on confocal mapping already cited here, which have been implemented in the laser scanning ophthalmoscopes now available on the market, such as those of Rodenstock Instrumente in Munich.

The separation of two beams by distinguishing their polarisation, as is described in connection with FIG. 6 of the 343 patent, in order to project an identical image into both eyes, is as a matter of principle an inappropriate method of displaying "genuine" three-dimensional images, since those images in this case do not have any differences in perspective. Furthermore, this method does not permit any dynamic and individual adaptation to the alignment of the eye and is therefore difficult to implement in technological practice.

In a second European application by Motorola Inc. No. 0 562 742 A1 entitled "Direct retinal scan display" from August 1993, a direct viewing image display apparatus is described, which, like the Sony patent described above, also relates to the direct transmission of images onto the retina, though with the difference that the projection is effected by deflection via a pair of spectacles worn by the person.

The system according to this prior art does not propose any possible solutions which are novel compared to the technology which has long been in existence. The direct fitting of the entire display on the head of the viewer in claim 4, and the method of deflecting the beam path of the projector via a pair of spectacles in claim 5 has already been marketed in the form of "virtual reality" spectacles and the head-up-display in pilots' helmets.

For the mapping on the retina to succeed, the laser beam deflection must satisfy various optical requirements, which demand not only a particular design of the beam control after the beam has been deflected, but also a special spectacle lens curvature. The ways to solve these fundamental optical problems are not considered or mentioned in the latter patent application, however.

The system of the invention proposes a serial capture and projection device, which makes it possible to capture the images of the outside world generated on the retina of the human eye during the natural process of visualisation and to modify them using electronic image processing. This image is then subsequently projected back into the eye using laser beam image projection and is synchronously superimposed on the original image. The invention further proposes that, both during capture and during projection, the radiation of all the primary colours red, green and blue is detected and projected.

This problem is fundamentally different from that of a confocal laser scanning ophthalmoscope, in which the retina is illuminated and mapped simultaneously in the same scanning process, because, in the arrangement according to the invention, the two-dimensional reflex image of the outside world is scanned in a first scanning cycle using the "flying spot" method, and it is only in a second scanning cycle, separate in time from the first, that the processed laser image is projected onto the retina. In a third scanning process the reflex image is captured again, in the fourth the laser image is projected again, etc. Since these processes take place in rapid succession, this gives rise for the eye, as when watching television or a film, to a continuous sequence in which the laser image follows the original image synchronously and congruously, irrespective of the eye movements.

The invention is also different from all the proposals known to the applicant for direct laser projection into the eye, both the projection of foreign images in closed spectacles (cyberspace), and the projection of the additional images in open spectacles (HUD), in that the present invention for the first time proposes directly coupling the projection to the content of the image of the outside world, and offers the novel technical means for implementing the proposal.

The capture and further processing of the retina reflex in the form of an image has become possible as a result of the rapid progress made in the capture of weak optical signals and the technology for processing them. The irradiance to which the retina is exposed in the natural environment ranges, with the brightest external illumination, between $10^{-4}$ W cm$^{-2}$ and about $10^{-7}$ W cm$^{-2}$. With weak internal illumination, under reading conditions, it ranges between $10^{-5}$ W cm$^{-2}$ and $10^{-6}$ W cm$^{-2}$ (see, for example, "Safety with Lasers and Other Optical Sources", D. Sliney and M. Wolbarsht, 1980). With a photon-counting photomultiplier and pin-point scanning with lasers in a TV standard, a sensitivity of up to $2 \times 10^{-5}$ W cm$^{-2}$ and a signal-to-noise ratio of 5 was achieved (see R. H. Webb et al., "Flying spot TV ophthalmoscope", Applied Optics, Vol. 19, No. 17, pp. 299 ff. (1980).

An increase in the sensitivity up to $10^{-7}$ W cm$^{-2}$ can be achieved, for example, by improved noise rejection, or reduced high-sensitivity resolution, or by using a spiral scan instead of the TV raster scan, which provides a reduced scan rate in the middle of the field of vision and thus a longer integration time.

Figure 1:
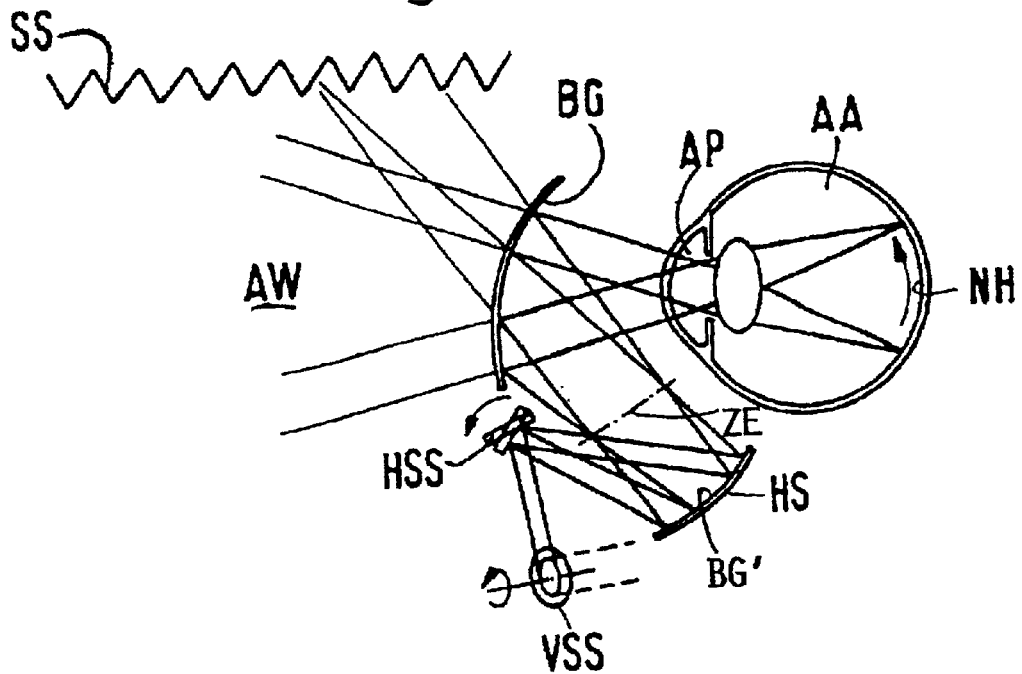
FIG. 1 is a schematic depiction of an embodiment of the device for capture and projection into the eye, wherein the mapping is effected between the scanner and the eye via the two concave reflecting surfaces of an auxiliary mirror HS and the internal surface of the spectacles BG.

Referring to FIGS. 3, 4, 7, 13 and 14, the present systems are used for ophthalmological/medical applications, for example, as a scanning capture device for the serial capture of the low-light reflex of objects from the outside world AW on the retina NH of the eye AA, as shown in FIG. 1 to FIG. 3. The same mapping and scanning device is also used to project the processed image onto the retina using lasers and image modulators in the opposite direction along the optical path, and with a time lag, as is also shown in FIG. 1 to FIG. 3.

Figure 5:
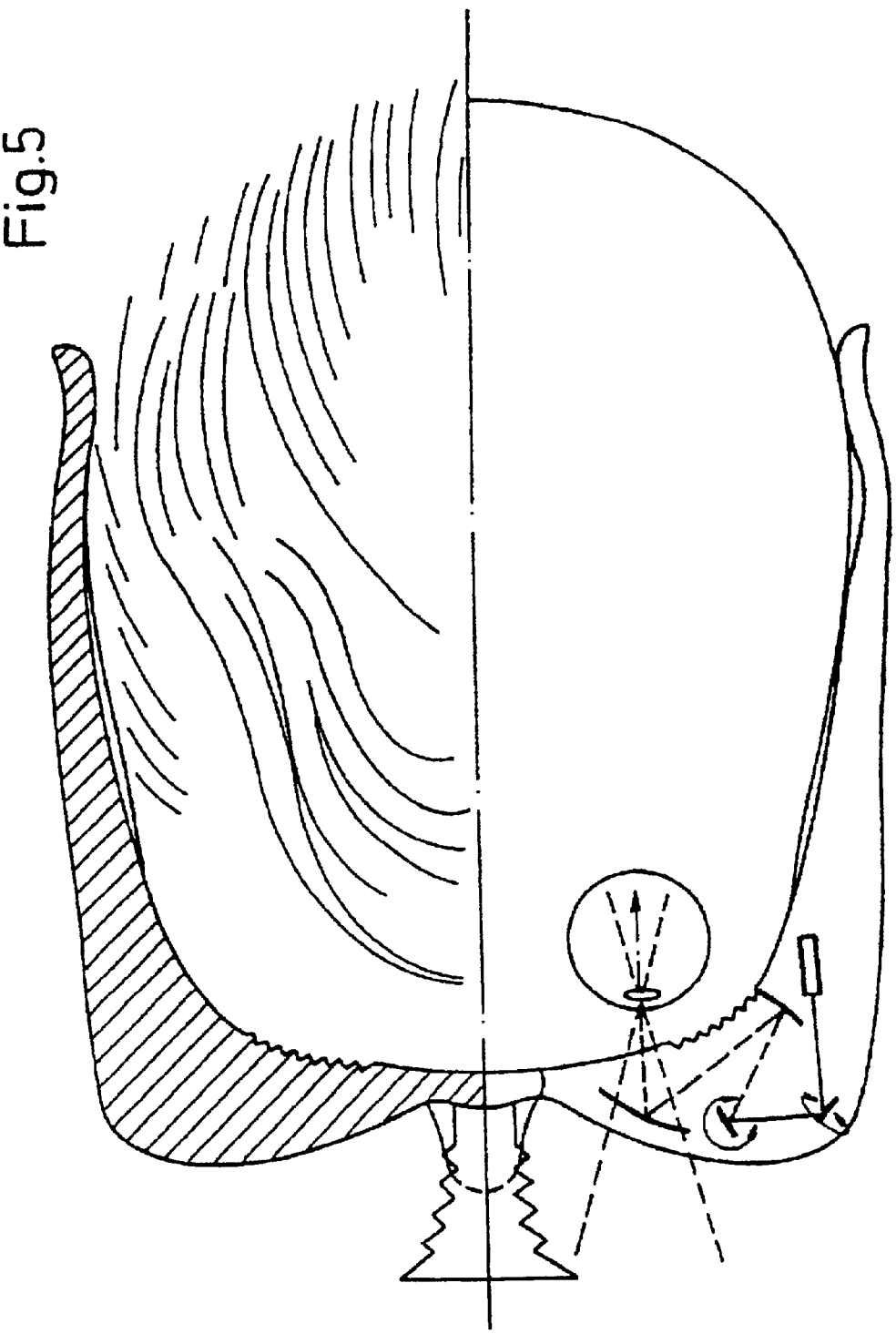
FIG. 5 is a schematic depiction of an embodiment showing how the binocular device for capture and projection is mounted in a spectacle frame.
Figure 6:
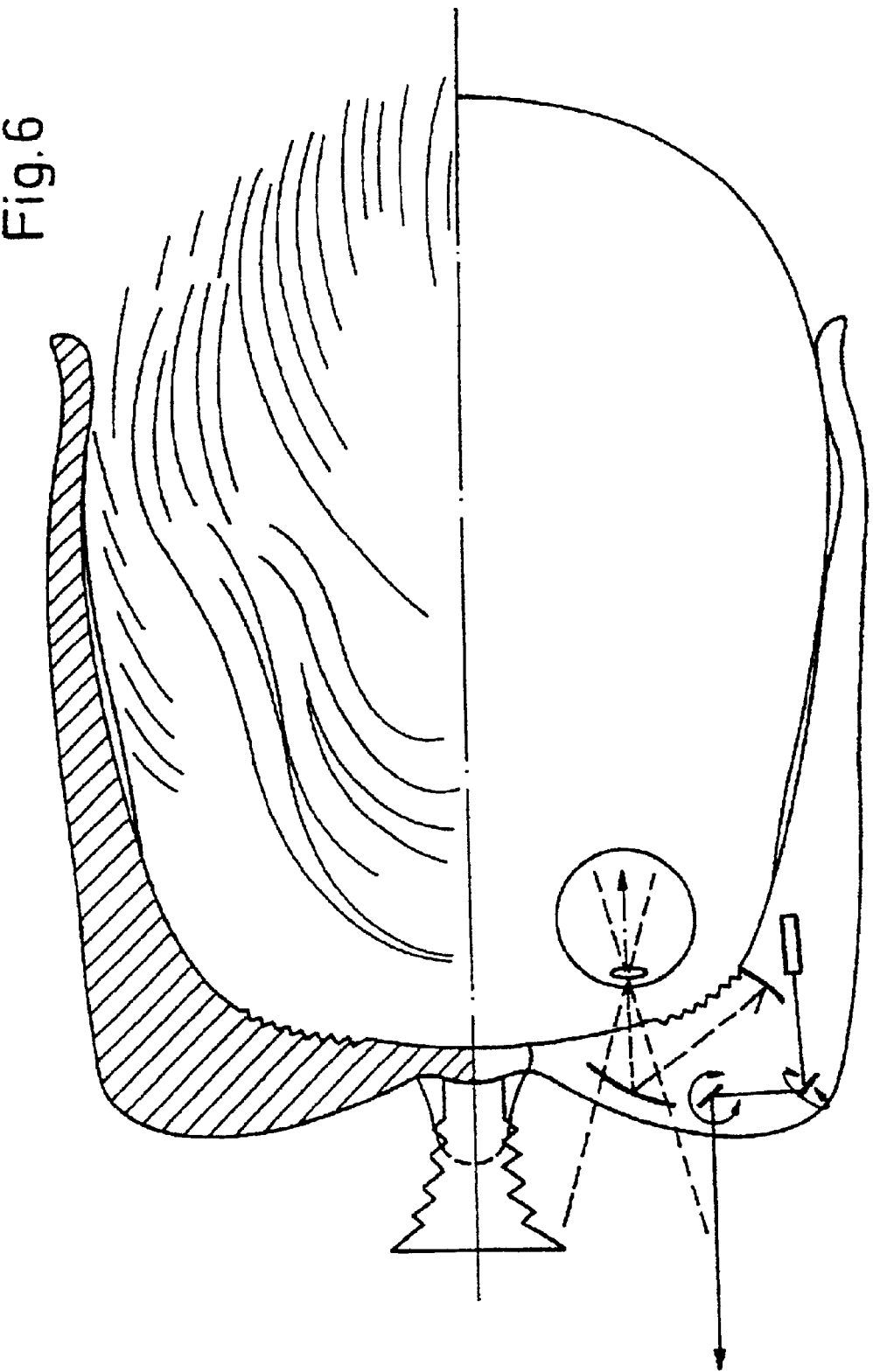
FIG. 6 is a schematic depiction of an embodiment of the beam path in the scanner when capturing the retina reflex and subsequently projecting the image onto the objects of the outside world by switching the horizontal scanning mirror over by an angle of 90°.
Figure 9:
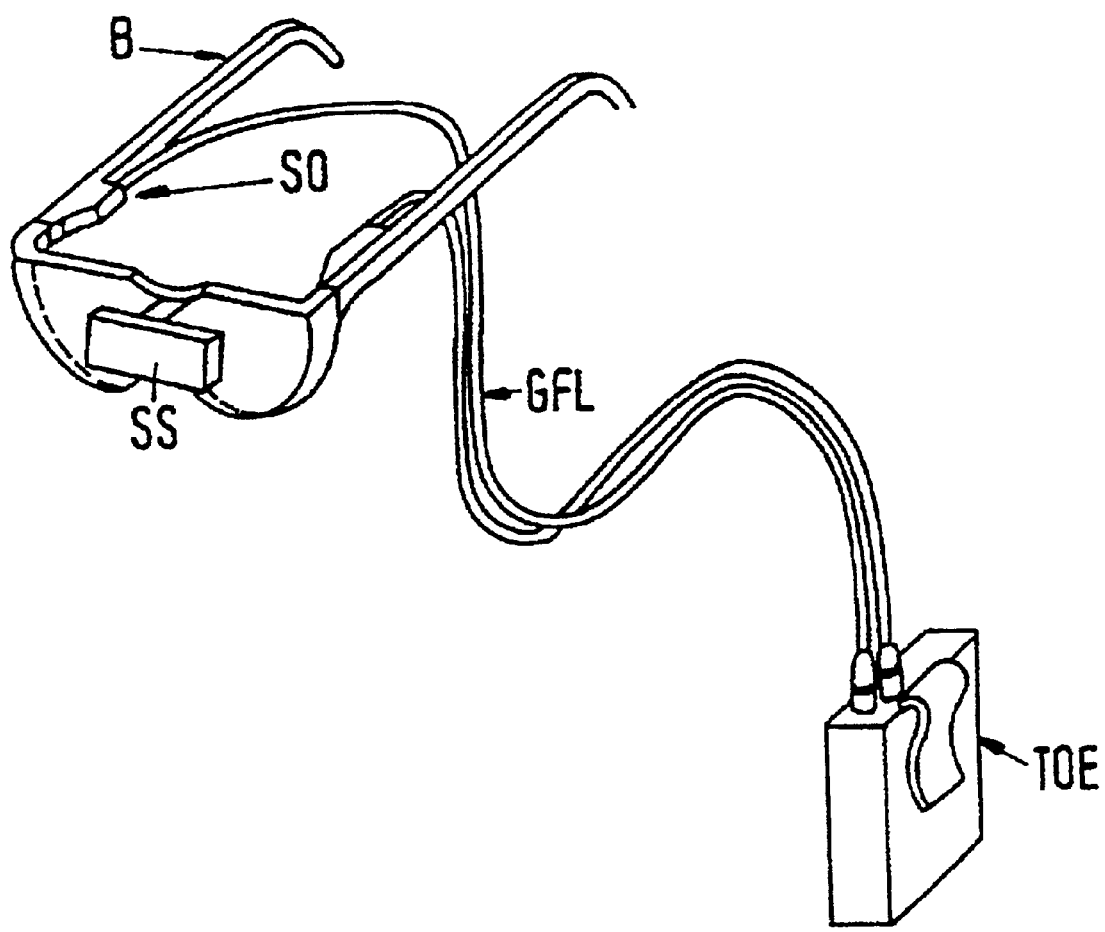
FIG. 9 is a schematic depiction of the scanner integrated into the spectacle frame in a micro-structure with a glass fiber coupling to a portable reception and projection unit and wireless transmission to the image processing computer.

Preferably, the described systems use a special pair of spectacles, which is worn by a viewer, as shown in FIGS. 5, 6, and 9. The spectacle lenses BG serve as beam splitters. They work as such both in transmission, for the light from the outside world, and in reflection, as an imaging surface for the light reflected back through the eye from the retina, which is delivered to a photo-electric receiver (FIG. 1 to FIG. 4) using further imaging elements and a two-axis scanner for horizontal HSS and vertical VSS deflection.

The beam path is at the same time designed in such a way that the extension of the line of sight from the detector through the spectacles always leads into the absorbing layer of a radiation sink SS. The extension of the line of sight from the eye through the spectacles, on the other hand, leads to the outside world AW (FIG. 1 to FIG. 6).

The simplest method of splitting the beam at the spectacle lenses BG is to use 50% transmitting and 50% reflecting mirror glasses. It is also possible to use active, electronically controllable mirrors, which switch from complete transmission to complete reflection in the two scanning cycles.

The eye AA maps parallel or virtually parallel focused beams from the outside world AW on the retina. The center of rotation of the focussed beams, when the outside world is seen from different angles, is located in the pupil AP.

The invention proceeds on the basis of the simultaneous capture and projection into both eyes, as is shown in FIG. 5 and FIG. 6, and thus of a largely identical beam path for the left and right eyes. In the case of persons with sight impairments, including different refractive power in the left and right eyes, the invention provides either for the spectacle lenses to be individually adapted in their refraction, using corresponding differences in the design of the curvature of the outer sides and the inner sides, or for contact lenses to be worn. For persons with normal sight, the curvature of the outer sides and the inner sides of the spectacle lenses BG is identical.

The light scattered back from the eye from each individual image point of the retina is similarly a set of parallel focussed beams, which travel along the identical path to that of the impinging light, in the opposite direction and strike the inner side of the partially reflecting spectacle lens BG. The curvature of this surface is designed in such a way that, together with the lens of the eye, a second image of the image point forms on the retina in the intermediate plane ZE (FIG. 1). An auxiliary mirror HS, collimates the beams again and maps them in such a way that they run via the common center of rotation (as on the other side through the pupil) on the axis of the horizontal scanner mirror HSS. Vertical deflection is effected by a second scanner mirror VSS.

Mapping from and into the eye using the two mirrors, auxiliary mirrors and spectacle lens mirrors, while at the same time allowing free vision through the spectacle lens BG to the outside world AW, requires a relatively great beam deflection. The deflection in the opposite direction via two concave mirror surfaces partially compensates for any mapping errors that occur in the process. The path of the beam in the opposite direction, which is otherwise identical, namely from the image capture and image projection, also largely avoids the formation of image distortions in the eye.

In the case of spherical mirrors, however, their major mapping errors mean that, despite the relatively small deflection angle required, namely <+/−10°, some residual image disturbances occur. For mapping and deflection into the eye, therefore, higher-quality mirror systems, such as concave parabolic mirrors and elliptical mirrors, may be used. An efficient reduction of the mapping errors is also possible with the aid of the mirrors at two concave surfaces BG and BG min and one convex surface HS. In this case, the second half of the spectacle lens with the same concave curvature as BG can be used as the full mirror surface BG min.

The invention assumes that any kind of two-axis image scanner can be used, such as, for example, revolving mirrors or polygonal mirrors for line deflection, and oscillating mirrors for vertical deflection or acousto-optical deflection units for both axes.

Using a raster-type scanning track with separate horizontal and vertical deflection, the image format can be designed to conform to the most common video standards, such as VHS, NTSC and HDTV.

It is, however, possible to use other scanning tracks, which are better adapted to the image format of the eye than raster scanning, such as spiral scanning, for example. The greatest visual acuity in the retina is located in the region of the fovea centralis, which, in the field of vision, only captures objects in a small angle range of about +/−2° around the visual axis. If a person's attention is directed towards an object, the eyes are normally moved in such a way that the beams proceeding from the fixed object strike the fovea centralis.

A spiral scan in the course of the image scanning process, in which the dwell time of the scanning beam increases continuously in the direction of the visual axis, would in this way be adapted considerably better to the structure of the retina than a raster scan. The longer dwell time also achieves a correspondingly higher signal-to-noise ratio in the middle range. For these reasons, apart from the use of a raster scan, the present systems also provide for the possibility, in addition, of using a spiral scan using a corresponding design and control of the two beam deflection units.

Similarly as in a laser-scanning ophthalmoscope, the beam path is split between the projection and receiving channel using a switching mirror SUS. Since the diameter of the projection beam can be made considerably smaller than the receiving beam, because of the good focusing and the small diameter of the laser beams, it is possible to use a perforated mirror to separate the two beam paths, as is shown in FIG. 3 and FIG. 4. A more efficient method, which results because of the alternating use of the two beam paths, is to use a tilting mirror, which switches over the beam paths synchronously with the scanning process. This solution has the advantages of lower optical losses in the receiving channel and better optical shielding of the direct cross-talk of the projection channel into the receiving channel.

Figure 7:
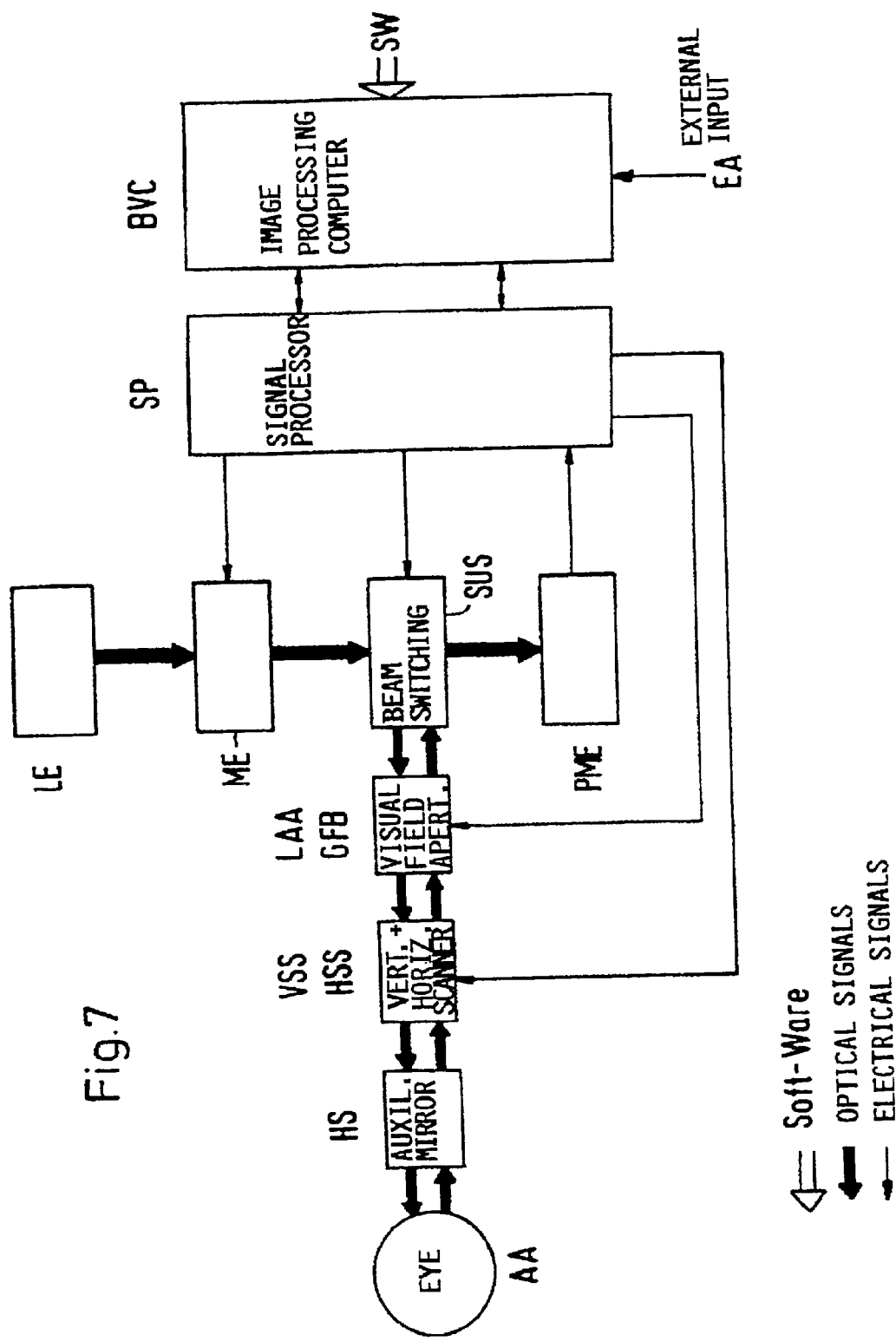
FIG. 7 is a schematic depiction of the opto-electronic and electronic sub-units and their connections.

In the beam path of the projection unit downstream of the beam switch SUS, as is shown in FIG. 3, the system includes a focusing device FE, which adjusts the size of the laser image spot and the scanned spot during reception GFB on the retina. In order to adjust the field of vision seen by the photomultipliers at any particular moment, the system includes a common field diaphragm GFB in the beam path of two lenses. The adjustment of the field diaphragms is necessary in order to adapt to the illumination conditions at the retina and to adjust the desired high-sensitivity resolution. It is provided for both adjustments to be performed automatically via actuators acting on commands from a computer, as is illustrated in FIG. 7.

The present systems enable the retina reflex to be split into as many as three color channels by using dichroitic filters (DFR, DFG and DFB) and three separate detectors (PMR, PMG and PMB) and thus for it to be possible to capture a largely undistorted color image. On the laser side, dichroitic beam splitters are likewise used to combine the beams from up to three lasers in the red, green and blue ranges of the spectrum (LR, LG, LB), after the separate image modulation of each color (MR, MG, MB), on a common axis.

In order to capture an image in true colors, the optical signal is broken down into the three color components with dichroitic filters DFR, DFG and DFB in the receiving channel upstream of the three photo receivers, preferably photomultipliers PMR, PMG and PMB, and, having been broken down into the three primary colors, these are measured separately. Since the light signals are weak, photon-counting methods will mainly be used.

The invention further provides for the electronic image captured by the detector to be converted back, after image processing, using laser beam sources and modulators, into a serial optical image, and, in a second image cycle using the same optical device—now functioning as a beam deflection unit (laser scanner)—after reflection at the inner surface of the spectacle lens, for it to be projected back into the eye synchronously with the scanning of the original image, though with a time lag.

Figure 8:
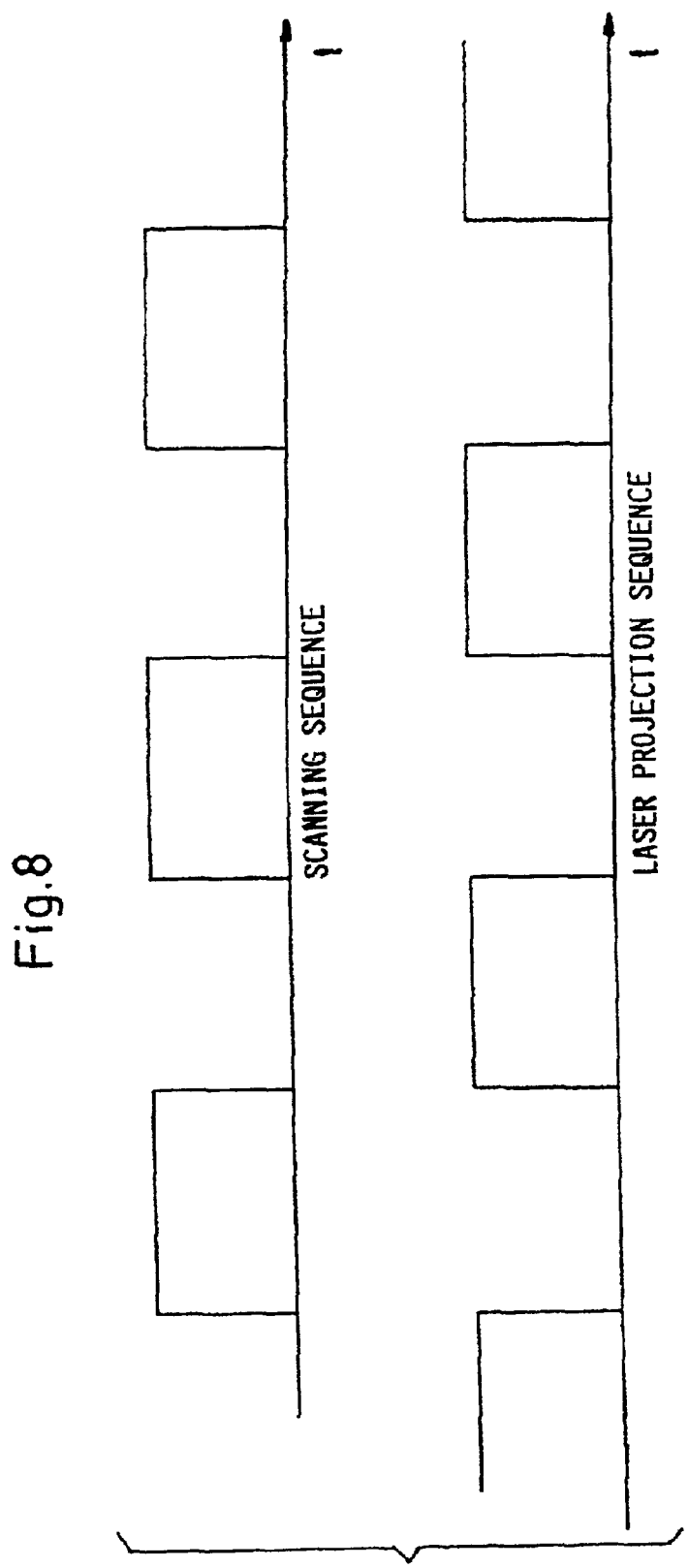
FIG. 8 is a schematic depiction of the sequence of the scanning and laser projection processes.

In the described systems the periods of image capture and image projection is preferably carried out separately in time, i.e. alternating, as is illustrated in FIG. 8. This timing avoids any interference with the capture of the weak retina image of the outside world by the projection, which is of a higher light intensity. In a first image cycle, for example, the retina reflex image is captured, and in the second, the processed electronic image is projected into the eye. In the third image cycle, the retina reflex image is captured, and in the fourth, there is a further projection back, etc.

If this image alternation is fast enough, the inertia of the sense of sight ensures that the two images appear to the observer to be superimposed on one another, provided that the time lag for the image inserted into the eye is less than the duration of the movement and perception time of the eye, and that the stability and resolution of the image inserted is comparable to the resolution of the eye.

So that both the involuntary rapid interrupted movements of the eye with of a mean amplitude of 5 arc minutes and a duration of between 10 and 20 msec, and also the rapid eye movements of 20°–30° per second when tracking a moving object can be detected over a large angle, the image refresh rate must be sufficiently high. With a refresh rate of between 50 Hz and 100 Hz, as in the field of television and computer engineering, the capture has been largely adapted to the most rapid movement processes of the eye. This applies both to raster and to spiral scans.

Other technical requirements to be met by the capture device relate to the size of the field of vision detected and the image resolution of the device proposed here. For most applications, the region of sharpest vision with a diameter of 10 and a number of 7 million cones (image points) in the fovea and also the adjacent region, with a substantially lower resolution of up to about 10° in diameter is of interest. For these different resolution requirements, precisely the spiral scan of the scanning track is particularly suitable.

The light sources suggested for projecting the images back into the eye are semiconductor lasers or miniaturised solid-state lasers with a low continuous-wave power (<300 $\mu$W), since these cannot cause any damage to the eye. By using semiconductor lasers, the image modulation could be performed directly via their power supply. So that all colors are generated, it is recommended to use three lasers with the primary colors red, green and blue. As the known color triangle of the human sense of sight shows, all the other colors and also the non-colours grey and white can be formed by the color summation of the monochromatic laser lines of those colors. The invention also comprises the possibility of using individual colors as a monochrome solution.

As is illustrated in FIG. 7, the system includes a signal processor SP, which processes the direct image from the retina electronically and synchronously co-ordinates all the functions of the device, the scanners VSS/HSS and the laser spot adjustment and the size of the field diaphragm LAA/GFB. The image processing computer BVC then takes over the image perceived by the eye or images from other technical sensors which are delivered to the computer via an external connection EA, and processes them using predetermined software SW, before they are modulated onto the laser beams as an image signal using the signal processor.

In addition to projecting into the eye the image currently being processed by the computer and merging it with the original image, laser projection also makes it possible synchronously to superimpose onto the image of the outside world in the eye foreign images which are delivered to the computer externally. If the time between the image capture and its projection is sufficiently short compared to the rapid eye movements, the eye, as when watching a television screen, will no longer perceive any interruption in the image.

The separate but simultaneous image scan on both eyes also detects the differences in perspective of the two images. Since the latter are preserved in both eyes when projected back by the laser, it is ensured that spatial vision is restored.

In addition to projecting the retina images back into the eye after image processing, one embodiment of the present system makes it possible to project these laser images directly onto the objects in the surroundings and seen by the eye. This embodiment is illustrated schematically in FIG. 6 by folding back the scanning mirror by an angle of 90°.

The present systems use various miniaturised components. For example, the beam deflection unit and scanner can be housed in a simple spectacle frame B, as illustrated in FIG. 9. The laser projection unit and receiver unit can be stored separately in a small housing TOE, for example the size of a paperback, with a battery power supply. The laser projection unit and the receiver unit are optically coupled by a glass fiber line GFL to the beam deflection unit and scanner. Data can be exchanged with a permanently installed external image processing computer either via radio waves or infrared rays. All the elements of the device of the invention could thus be procured by anyone with no difficulty according to the current state of the art, and the wireless exchange of image data with the external computer would permit that person's unrestricted freedom of movement.

In addition to the applications in the fields of medical engineering/ophthalmology and strabology/neuro-ophthalmology, there are also a number of additional uses of the system described above.

These uses are described in detail in patent application DE 196 31 414 and can be summed up in the following four categories:

(a) Capturing images of the outside world, processing them, projecting them back and merging them with the original image in the eye.

(b) Superimposing images from other capture systems, such as ones of the same scene but in different ranges of the spectrum, onto the direct image.

(c) Superimposing virtual images which have been produced by the computer alone.

(d) Capturing images of the outside world and projecting them by laser not into the eye, but onto the same objects of the outside world which are seen by the eye.

The first category comprises applications with the aim of improving the image captured by the eye by targeted image summation, for example focussing and enhancing a blurred or low-light image, which would be of great assistance to people with impaired sight, and also for those with normal sight.

Other possible image alterations would, for example, be changing the colour of objects by a new color summation. This technique could be used to deliberately stain white certain areas of the field of vision, and thus to delete or reduce the optical information.

The second category consists in superimposing images of the same scene, for example from the invisible infrared range or from radar devices. This technique would, for example, make it easier to drive or fly by night and in fog or mist.

In medical applications, for example, X-ray images, acoustic images and images from NMR tomography could be superimposed on the direct image of the patient's body or his organs to assist the physician in diagnosis and surgery.

The third category comprises applications in which the image is supplemented by virtual additional inserts, such as in the applications found in current HUDs for driving vehicles, for example. The invention offers the additional advantage of the precise synchronisation between the insert and the external image. In this way, foreign images could be inserted on precisely defined empty parts within the direct image, such as those with little image content, for example, or as a stereoscopic image at a different distance from the other objects.

This third category includes interactive applications from computer technology, i.e. the insertion of a virtual computer mouse (cross-hairs), which is moved across real objects in the outside world (also a display) with eye movements alone (instead of with the hand). In this case, a click or a command could be executed by additional eye movements, such as a blink of the eyelid, or by a verbal command or the touch of a key.

This third category also includes cyberspace applications, i.e. the insertion of complete virtual computer images into the closed spectacles. With the aid of the invention, scans of the retina image of the virtual images inserted could be used to stabilise the latter against the eye movements.

The fourth category describes a kind of "active vision", i.e. a scene seen by the eye and captured by the scanning device is serially illuminated in the next scanning cycle with a laser image light projector. This scene thus illuminated is perceived by the eye again and, in the subsequent cycle, leads to an altered second laser illumination process, which is followed by a third processing step, etc.

In this way, a closed optical loop comes about, which can be used, using an appropriate arrangement of the illumination, as a positive or negative loop for the most varied applications, such as to brighten objects which are only faintly distinguishable, to enhance their contrast, or to change their colour.

Figure 10:
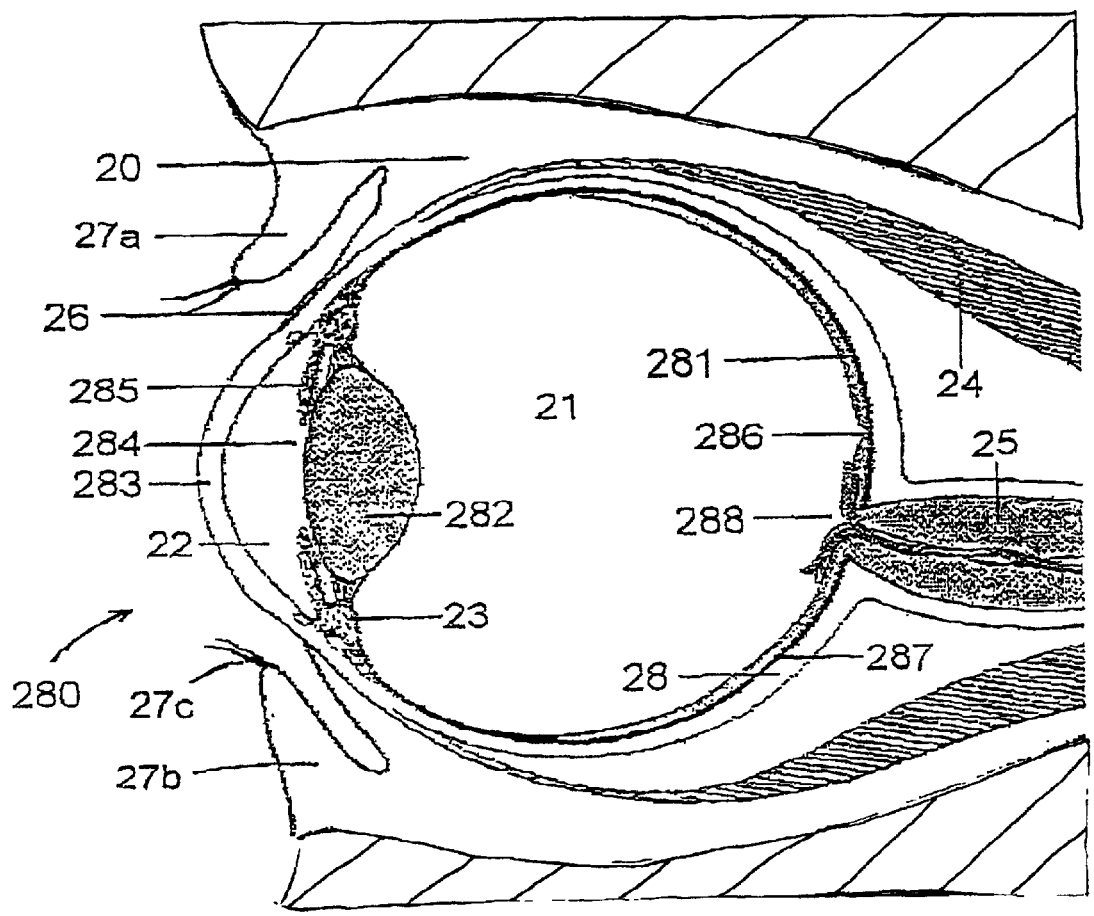
FIG. 10 is a schematic section view of the human eye intended to explain the fundamental ophthalmological facts.
Figure 12:
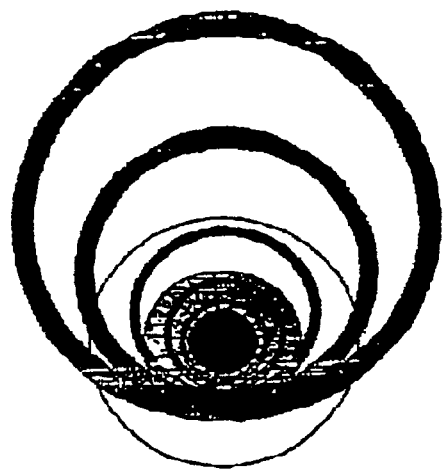
FIG. 12 shows the search mode of centering the scan through the pupil.

For better understanding, FIG. 10 shows a detailed view of the eye 280 in cross-section. The eye 280, which is housed in the eye socket 20 (Lat. orbita) formed from skull bone in a person's head and should here be understood in the sense of an eyeball 280, consists of a chamber surrounded by a light-permeable cornea 283 and a visibly white sclera 28. On the side facing the interior of the eye 280, the sclera 28 is covered by a choroid membrane 287 (lat. choroidea), which on its own inner surface in turn supports a light-sensitive retina 281 and supplies it with blood. By means of its pigmentation, the choroid membrane 287 prevents the impinging light from being scattered, which could impair a person's vision.

The tissue of the retina 281 comprises two kinds of photoreceptor cells, namely rods and cones (neither shown), which enable a human being to see. These photoreceptor cells absorb the light focussed by an eye lens 282 in a wavelength range from approx. 380–760 nm and convert it using a series of chemical reactions into electrical nerve signals. The signals from the various nerve cells of the retina 281 are then transmitted to the brain via the optic nerve 25 and are processed there into a perceivable image. The numerous rods, of which there are approx. 120 million and which are extremely light-sensitive, are specialised in capturing signals in twilight and provide a grey-stage image. On the other hand, the cones, of which there are approx. 6.5 million and which are less light-sensitive by comparison, are responsible for processing in daylight and for color vision. In the course of the light absorption, oxidation of pigments in the photoreceptor cells occurs. In order for the pigments to be regenerated, the cones take approx. 6 minutes and the rods approx. 30 minutes. An observation period of approx. 200 msec is required in order for the visual stimulus via the photoreceptors to begin and for information capture via the retina 281 to occur.

The retina 281 has an indentation 286, which appears somewhat more heavily pigmented because of its greater density of cones compared to the rest of the retina. This indentation 286, which is usually referred to as the fovea 286 (fovea centralis), is located in a region of the retina known as the "yellow spot" (Lat. macula) and is the region of sharpest vision. The fovea centralis 286 only has cones, with a very high cone density, and takes up no more than about 0.01% of the surface of the retina. At the point opposite the lens 282 indicated by reference numeral 288, the optic nerve 25 passes through a sieve-like opening in the sclera 28 and enters the interior of the eye. This point 288 has no photoreceptor cells, which is why it is referred to as the "blind spot".

The chamber formed by the cornea 283 and the sclera 28 is subdivided by a deformable lens 282 and a muscular ciliary body 23 (also known as the corpus ciliare), which holds the lens 282. That part of the chamber located between the lens 282 and the retina 281, which makes up about ⅔ of the eyeball, forms what is called a vitreous body 21, a gelatinous structure which consists of more than 98% water and which supports and protects the retina 281. That part of the chamber referred to as the anterior chamber 22, which is located between the cornea 283 and the lens 282, contains a fluid that nourishes the cornea 283. In its original form, the lens 282 typically refracts the light impinging on the eye in such a way that the distant field of vision is projected in focus onto the retina 281. When the muscles of the ciliary body 23 are contracted or relaxed, the shape and thus also the refraction characteristics of the lens 282 can be varied over a wide range in order, for example, to permit the focussed projection of nearby objects in the field of vision onto the retina 281. In most cases, this process takes place without the person concerned being aware of it.

Immediately in front of the lens 282 in the anterior chamber 22, there is a diaphragm 285 of variable diameter, consisting of colored tissue, which regulates the amount of light admitted to the light-sensitive parts of the eye 280 and which gives the eye 280 its characteristic colour. This diaphragm 285 is known as the iris 285. Because of the small amount of light scattered back by the lens 282, the vitreous body 21 and the retina 281, the central portion of the iris 285 appears black, and this part is referred to as the pupil 284. The regulation of the size of the pupil likewise takes place without the person concerned being aware of it.

The eye 280 is joined to the skull by six muscles 24, some of which run parallel, and others diagonally to one another, and which allow the eye 280 to swivel, thus permitting the line of sight to be altered. The binocular field of vision encompassed without moving the eyes 280 covers approx. 170° horizontally and approx. 110° vertically. When the eyes 280 are moved, a binocular field of vision of approx. 290° horizontally and approx. 190° vertically can be covered. The region of sharpest vision detected by the fovea centralis 286 encompasses only about 1°. A theoretical axis running through the middle of this region is referred to as the visual axis and corresponds to the line of sight. The muscles 24 also make it possible to rotate the eye about the visual axis.

The six muscles 24 are responsible for all eye movements. When a fixed point is being observed, microtremors occur in the eye 280, in which the eye 280 trembles slightly in order to avoid a temporary exhaustion of the chemical reactivity of the photoreceptor cells concerned when the stimulus remains unvarying. During a change in the line of sight or a head movement, interrupted movements, or "saccades", occur, by means of which the fovea centralis 286 is directed towards the new point on which it is supposed to concentrate, or the point on which it has been concentrating so far is maintained. In the course of this very complex movement, the eye 280 is involuntarily moved to and fro with a small amplitude of up to some tens of degrees and at an extremely rapid angular velocity of up to several hundred degrees per second. When tracking a moving object, the eye 280 reaches angular velocities of only one to two hundred degrees per second.

To protect the eyeball 280, the human body has movable folds of skin, namely an upper lid 27a and a lower lid 27b, which make it possible to seal off the eye socket 20 against external influences. The lids 27a and 27b close by a reflex action if foreign bodies penetrate, and when the light is very dazzling. Usually, the lids 27a and 27b involuntary blink to distribute evenly a film of tears over the cornea 283, and this rinses is the outer surface of the cornea 283 and prevents it from drying out. The lids 27a and 27b also have eyelashes 27c, which likewise protect the eye 280 against dust. A membrane of connective tissue 26 lines the space between the lids 27a and 27b, the eye socket 20 and the eyeball 280. The membrane 26 passes over on the one hand into the inner side of the lid, and on the other hand into the cornea 283, and constitutes a second line of defence against the penetration of germs and foreign bodies.

Additional information regarding the eye and the optic nerve is provided in "Clinical Ophtalmology: A Systemic Approach" by Jack J. Kanski (published by Butterworth-Heinemann); "The Retina" by Stephen J. Ryan (published by Mosby-YearBook); and "Atlas of Clinical Opthalmology" ed. by Roger A. Hitchings et al. (published by Gower-Mosb) all of which are incorporated by reference for all purposes.

The present system for capturing the retina reflex image may use spectacles, or other embodiments, for capturing the retina reflex image of the eye electronically via a reflection on the inner surface of the spectacles. When the brightness of the surroundings varies the retina reflex image can be modified with a computer and, using an illumination device and reflection back via the same spectacles, is superimposed on the original image with no physiologically perceivable delay, in such a way that an improved visual impression arises.

The use of opto-electronic spectacles to reflect computer-generated images into the eye, known as "cyberspace" or "virtual reality", is expanding rapidly today. There are a broad range of uses for this technique, both for application in the entertainment industry and in a wide range of fields of industry, transport and medicine, and these will become more and more widespread and important as faster and faster image processing computers become available.

The most widespread application is the use with closed, non-transparent spectacles, in which images are delivered to the eye by miniaturised cathode ray tubes or liquid crystal matrices via mirror or glass fiber systems. The special attraction of this technique is to use a moving three-dimensional graphical representation to link the sequence of images or the action to different movements by the person wearing the spectacles. A change in the line of sight, for example, is produced by a head movement, or a change in perspective is imitated as the wearer moves forwards. The movements of the wearer's arms and fingers can be integrated into the image by means of sensors, in order to enable him to intervene directly in the action.

In more recent systems, known as "augmented reality", the person wearing the spectacles can, by using partially transparent spectacles, observe both his surroundings and an image of the same scene or with different image contents which is reflected in via the spectacles by cameras and a miniaturised monitor on the helmet. A well-known version of this process has already been introduced in the form of piloting fighter planes, where it is known as a helmet-mounted display (HMD).

In these techniques, however, numerous problems are known, which are due to the way in which the sense of sight works, and which are waiting for improved technical solutions. In the case of closed spectacles and a rigidly coupled monitor and monitor image, when the person wearing the spectacles moves his head, the scene moves in the same direction, which is contrary to his customary vision and is thus unnatural. The way in which the eye captures a scene means that he is used to seeing the scene move in exactly the opposite direction. Up to now, it has only been possible to solve this problem imperfectly by mans of a complex process of measuring the head movement and the eyeball with external sensors which sensed the angle of rotation, with corresponding image processing and the need to adjust the image generated.

The eye itself is capable of roughly stabilising the retina image by means of movements to adjust the eyeball, which originate from so-called vestibular ocular reflexes (VOR) of the semicircular canal system of the ears and serve to retain the fixation point in the case of head movements. The fine adjustment is carried out with the image as the reference. This image tracking is used in addition by the eye in order to adapt the VORs to a dynamic eye alignment.

This means that any superimposition of foreign images cannot provide a realistic image impression until they are coupled to the real retina image.

In the case of closed spectacles, attempts have been made to use the image of the blood vessels (in the fundus of the eye) as the reference (retina tracking). This, however, only yields inadequate resolution and is suitable solely for monocular observation (see, for example, E. Peli, "Visual issues in the use of a head-mounted monocular display", Optical Engineering, Vol. 29, No. 8, p. 883 (1990). Simultaneous stabilisation of images with the eyes, in both eyes, is virtually impossible because of the different alignment of the eyes. Apart from the deterioration in the image quality, the conflict between the vestibular and visual information often leads to motor disturbances, even going as far as sea-sickness. These problems involved in the existing state of the art are described, for example, in the review article by E. Peli, "Real Vision & Virtual Reality" in Optics & Photonics News, July 1995, pp. 28–34.

The problems of image stabilisation when foreign images are superimposed on the real image are solved with the modified system shown in FIGS. 11 to 14. The embodiments of FIGS. 11 to 14 build on and further improve the process described in connection with FIGS. 1 through 9 for improving the perception of the eye. The physical and technical problems which have to be solved for this purpose are a consequence of the physiological properties of the eye and the constant variations in the illumination conditions in the surroundings. Because of the variable lighting conditions and the different optical tasks to be performed, the eye is a very dynamic sense organ in its basic functions. It adapts to the variation in the intensity of the background lighting over 12 decades. It changes over from color vision in daylight to pure black-and-white vision at night. Light in the wavelength range of 400 nm to 1500 nm is transmitted by the eye and focussed on the retina. And yet, only light in the range from 400 nm to 750 nm is perceived, i.e. the infrared light in the range from 750 nm to 1500 nm, which is very bright both in outdoor and in indoor lighting, remains unused for visual perception.

Horizontally and vertically, the eye covers an angle range of about 100°. The image resolution, however, declines very rapidly as the distance of the angle from the visual axis increases. Attentive vision at any particular moment is limited to a central angle range of only +/−5°, and "sharp" sight, for example when reading or driving a car, is restricted to the very small central angle range of +/−0.5° Furthermore, a wide variety of eye movements are constantly taking place. This leads to the following consequences, which, under certain circumstances, impair the perception of the eye and which it is intended to improve in the context of the present invention:

Adaptation, accommodation, focussing capacity, sight defects, reduced performance due to old age, and movement dynamics.

The embodiments of FIGS. 11 to 14 enable, like the eye in its basic functions, very variable and adaptable vision or visualisation. Furthermore, these embodiments also take into account and exploit the specific physiology and dynamics of the eye and the varying lighting conditions in the surroundings at the invisible to IR range.

One fundamental problem of serial compared to parallel image scanning is the short dwell-time of the scanner in each pixel. A smooth scan of, for example, 0.5 million pixels in a scanning time of 40 ms means an integration time of only 0.08 μs i.e. 80 ns in each pixel. By way of comparison, the parallel time integration of all the image points in the eye itself takes 10–20 ms.

As is known from the use of lasers to capture the retina structure of the eye in laser scanning ophthalmoscopes, a laser power of about 40 μW is needed in order to achieve a signal-to-noise ratio of 17 from one pixel in a raster scan (see, for example, A. Plesch, U. Klingbeil, and J. Bille, "Digital laser scanning fundus camera", Applied Optics, Vol. 26, No 8. pp. 1480–1486 (1987)). Extrapolating this to apply to the larger surface area, this would amount to an irradiance of 40 W/cm$^2$ in an image from an extended source on the retina, which corresponds to the irradiance of bright spotlights or the sun on the retina, i.e. with raster scanning only relatively bright sources can be recorded on the retina with a good signal-to-noise ratio. If mapping from weaker sources is to be detected on the retina, the sensitivity needs to be increased substantially.

For capturing the retina reflex, on the other hand, serial image scanning has the decisive advantage of better suppression of scattered light, simpler capture optics and the possibility of exactly reversing the beam path in projecting the image back with a laser, and for these reasons it will also be retained in this application. An extension of the dwell time can also be achieved, however, by altering the scanning pattern.

Because of the irregular distribution of the photoreceptors, with the greatest density of cones for sharp vision in the center of the retina and the opposite arrangement of rods for less sharply focussed, but light-sensitive, night vision, raster scanning is by no means the ideal scanning pattern. A scanning pattern adapted to the visualisation process ought to become slower and more densely packed towards the center for day-time vision, but precisely the opposite when adapted to night vision.

Apart from by the dwell time, the signal captured can also be influenced by varying the size of the spot scanned and thus also the image resolution.

The number of signal photons Ns per pixel which are captured from the retina by a scanning capture device can be calculated according to the following formula: $Ns=(B\,T\Delta\lambda\tau)(AoR)(S/2)(Ap/De^2)(1/\epsilon)$ where B=the spectral irradiance on the retina, T=the optical transmission from the retina to the photodetector, τ=the integration time in a pixel on the retina, Ao=the surface area of the pixels, R=the reflectivity of the pixels, Δλ=the spectral width of the receiving signal, Ap=the pupil surface area, D=the distance between the pupil and the retina, S/2=the angle distribution factor of the optical backscattering from the retina, and ε=the energy of a photon on the capturing wavelength.

As this formula shows, stronger signals, i.e. a larger number of signal photons, can be obtained by means of the following measures performed on the capture device: Extending the dwell time τ of the scan in the individual pixels, increasing the size of the scanning spot Ao on the retina, increasing the spectral bandwidth Δλ.

The embodiments of FIGS. 11 to 14 can scan the retina in a sequence of concentric circles (the center of the circle is identical to the fovea centralis), the radius of which is successively increased or decreased. This type of scanning is referred to as circular scanning. Because of the rotational symmetry of the lens of the eye and the pupil about the visual axis and the rotationally symmetrical distribution of the photoreceptors in the retina, circular scanning is ideal. The system can use an identical circular scan for capturing the retina reflex of the surroundings and for image projection with the laser. Since, in the case of a circular scan from the outside to the center, once the center has been reached, the axis of the scan returns back along the same path, there is the option of capturing during the scan towards the center and projecting from the center outwards, or capturing during the entire scanning process and only projecting in a second pass.

With a constant movement of scanning mirrors in two directions (Lissajou figure), the dwell time inevitably slows down towards the center in the case of a circular scan. The system can also slow down the scanning duration of adjacent circles even further for daylight vision, depending on the lighting conditions, and even to accelerate it for night vision. Because of the irregular distribution of the cones across the retina, with a density that is more than two decades greater in the center, the scanning rate (dwell time per pixel) can be increased by that factor, namely 100, in this region. For night vision, with the greater distribution of rods as the radius increases, it is a good idea for the opposite to happen and for the dwell time to decline to a similar extent as the scan moves outwards.

As known in the art, a circular scan can be performed with an analogue drive, using periodically oscillating orthogonal scanning mirrors, or with a digital drive, by approximating a circular track with a large number of straight sections. As a third alternative, there is the possibility of using programmable algorithms of analogue drive signals, which can be called up digitally and which are the best suited to these variable conditions.

So that the receiving signal can also be further enhanced by enlarging the scanned image spot, proportionally to its area, the invention further provides that the image pixel size on the retina at any particular moment can be variably adjusted in addition to the scanning rate. As the size of image spot changes, so the image resolution is adapted to the situation accordingly. Apart from changing the scanning surface, the resolution can also be adjusted by varying the radial pitch of the scanning radii.

If the scanning pixels are enlarged from, for example, 10 $\mu$m to 100 $\mu$m, the image resolution, for example, is reduced by a factor of 10 from about 2 to 20 arc minutes (resolution range for reading and looking at an object), while at the same time the signal received is amplified by a factor of 100.

As the man skilled in the art knows, the image resolution in the case of confocal scanning is determined by the diameter of the diaphragm in the intermediate focus upstream of the photodetector and can be adjusted by varying the latter. The invention provides that liquid crystal diaphragms or electro-optical diaphragms should be used for this purpose, so that such an adjustment can be performed as quickly as possible, i.e. within one scanning cycle.

Since the time taken for a scan and the size of the image pixels during capture and projection should as far as possible be identical, the invention proposes that the change in the time taken for the scan and the adjustment of the diaphragm in the projection channel is the same as in the receiving channel. The variation in the optical integration time and the image pixel area can then be compensated for in the projection channel by means of a corresponding variation in the laser's transmitting power.

The level of the receiving signal is also dependent on the spectral bandwidth of the receiver and can be raised by increasing the latter. The invention provides that, in the region of brightest daylight vision (photopic vision), it is possible to divide the beam path into the colour channels red, green and blue with a spectral width of about 100 nm in each case, corresponding to the color sensitivity of the eye. This makes it possible to capture images in true colors and to project images back into the eye with appropriate three-colour lasers.

When the ambient light is weak, which is when colours are no longer perceived by the eye (scotopic vision), the invention provides for all the channels to be combined into a single (black-and-white) receiving channel with no color resolution. In addition, the invention provides that this receiving channel encompasses not only the visible range of 400 nm to 700 nm, but also the near infrared range of 700 nm to 1000 nm.

The above arrangement offers the following benefits to enhance the receiving signal when the background illumination is weak: The eye is completely transparent between 400 nm and 1000 nm and maps an image between 700 nm and 1000 nm which is comparable to that mapped between 400 nm and 700 nm. The degree of reflection of the retina between 700 nm and 1000 nm is R=10–20% compared to R=3–5% between 400 nm and 700 nm. Photo-electric receivers with a high quantum efficiency and also photomultipliers and silicon avalanche diodes over the entire spectral range from 400 nm to 1000 nm are available. Light bulbs which are used to illuminate the interior of buildings, or for street lighting in the open air and in vehicles, radiate 10 times as much light between 700 nm and 1000 nm as between 400 nm and 700 nm. The reflectivity of natural vegetation is higher by a factor of 5–10 between 700 and 1000 nm than between 400 nm and 700 nm.

As these examples show, when the light is poor (night vision), it is possible to enhance the receiving signal even further by a factor of 100 by expanding the spectral range.

The expansion of the spectral range can either be permanently installed in each device or it can be made variable by replacing spectral filters. If color representation is not required, it is a good idea to use green laser light for projection back into the eye, because of the eye's greatest sensitivity and contrast perception with this colour.

Additional methods for improving the signal which can be used here are the integration of a number of successive images and image correlation, such as images from both eyes.

All in all, by varying the two parameters, namely the dwell time of the scan in the pixels and the size of the image spot, and by adding the infrared range and using image correlation, a total dynamic response of the receiving signals can be detected over seven decades.

With a total optical transmission of the receiving channel of T=0.2 (see formula above), the receiving range of this dynamic capture system encompasses irradiances on the retina of between $10^{-5}$ W/cm$^2$ and 100 W/cm$^2$, which comprises the range of typical indoor and outdoor brightness.

Because of the slow and rapid eye movements, it is necessary to design the scanning system in such a way that it constantly follows the change in the visual axis through the spectacles, i.e. to ensure that the axis of symmetry of the image scan is identical to the visual axis both during capture, and during projection.

The embodiments of FIGS. 11 to 14 enable centering of the circular scan on the pupil before and after the scan of the retina reflex or the image projection into the eye. In the process, the greatest scanning angle of the circular scan is selected such that, if the axis of scanning symmetry is out of alignment with the visual axis, the outer surface of the eyeball, the sclera, the iris and the pupil are detected by the circular scan. Since these parts of the eye, which are well illuminated by the external light, are not mapped in focus, but diffusely in the intermediate image plane of the photodetector, the receiving signal does not in this case supply any image information, but an integral display of the optical back-scattering capacity of the original.

Figure 11:
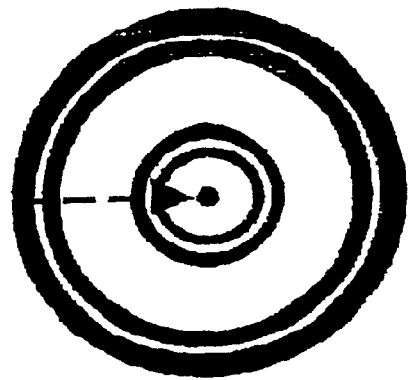
FIG. 11 shows schematically the concentric scanning process with the system adjusted in accordance with a variant of the system.

When the receiving signals from each circle are compared over sections of identical length, such as quadrants, they are only the same height if the axis of the circular scan is identical to the axis of the eye (visual axis). Signal differences because of the different backscattering from the sclera, iris and pupil are then a measure of the degree of misalignment and its direction. After standardisation with the entire receiving signal over each circle, these misaligned signals can be used to set the zero position of a next circular scan (bias). In this way, an original misalignment of the axes can be reduced with each circular scan until it becomes negligible when the circular scan passes through the pupil (pupil tracking). FIG. 11 schematically illustrates the concentric scanning process in an adjusted system, while FIG. 12 demonstrates the search mode for centering the scan through the pupil.

As an alternative to using the ambient light, the invention also provides that it is possible to use active illumination by laser projection into the eye to carry out pupil tracking in the outer regions of the circular scan, with simultaneous signal evaluation in the capturing channel, as described above.

The invention further provides that the light scattered back both by the surroundings and by the laser is also captured and evaluated during the laser image projection. This simultaneous capture of the retina reflex of the surroundings and post-processing laser image projection opens up the possibility of constantly monitoring the degree of overlapping and the time synchronisation of the two images and detecting possible differences as image interferences (moiré pattern), in order then to compensate such differences by subsequent correction signals.

The capture and projection technique for the purposes of the invention can either be performed on one eye of an observer or on both his eyes at the same time, independently of one another. Because of the stereoscopic vision achieved with two eyes, three-dimensional image capture and image reproduction is obtained in the latter case.

Figure 13:
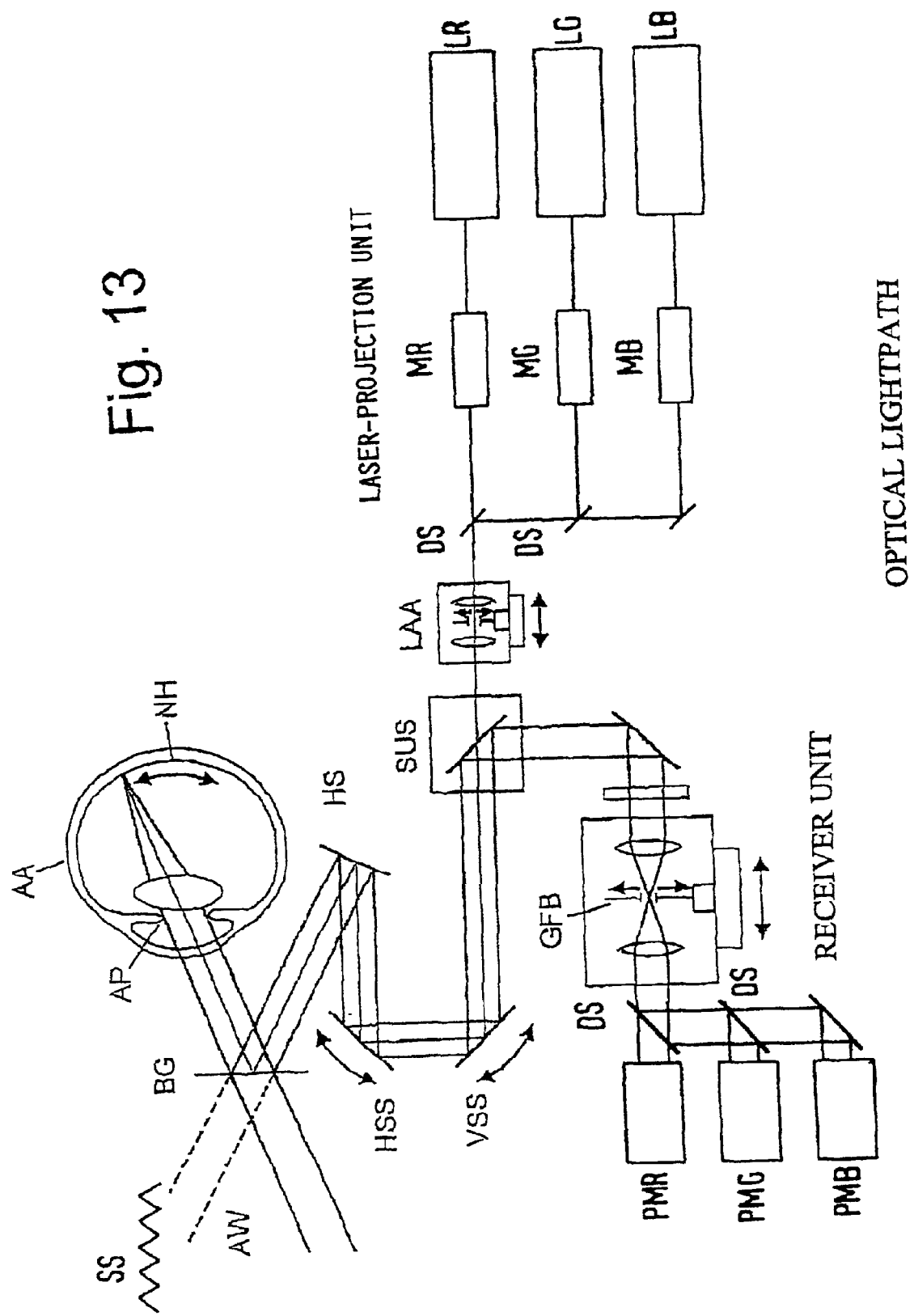
FIG. 13 shows schematically an overview of the entire system.

It is not readily comprehensible that the capture of an error-free and distortion-free reflex image of the surroundings by the retina can be possible with spectacles whose optical properties are not individually adapted to each wearer and which are likewise not mounted completely stably on the wearer's head. The solution to this problem for the purposes of the invention consists firstly in the relatively minor optical requirements to be met by the serial confocal pin-point scan, compared to two-dimensional mapping from the eye, for example, secondly in the complete dynamic adaptation of the optical beam path of the scanner into the eye by means of the spectacles, which take into account the independent movements of the eye and the spectacles themselves every time, and thirdly in the exact reversal of the beam path between capture and projection and the short time between these processes. For the purposes of adjusting the scan through the eye, even when the eye movements are different, there are two scanning elements and a correction mirror, which can also be adjustable. FIG. 13 shows a schematic overview over the entire system. The retina of the eye NH is scanned with the focussed beam. In this case, AA indicates the eyeball and AP the pupil. The partially transparent spectacles are indicated here by BG.

The beams passing through from the surroundings are focussed on the retina, and at the same time the retina is scanned point by point, the scanning beam always being directed towards a radiation sink when being transmitted through the spectacles. The two-axis scanning elements HSS and VSS are used to perform the circular scan. The auxiliary mirror HS, which can be actively adjusted, is used to adjust the direction of impingement and the position of the beam on the inner surface of the spectacles BG. With the beam switch SUS, it is either possible, with a central hole, to allow the illuminating laser beam to pass through and to ensure that the receiving beam, which is usually substantially larger in diameter, is reflected directly into the receiver unit and is conducted in separate directions, or an actively switching mirror element can be used, which switches between reception and transmission.

The receiver unit can, for example, consist of three separate receiving channels for the primary colors red, green and blue, or other wavelength ranges, such as in the near infrared range. The beam path of all the spectral channels is placed on an axis with the aid of dichroitic mirrors DS. In order to adjust the size of the spot from the scanning beam on the retina and optionally to make minor corrections to the optical axis, there is an actively adjustable field diaphragm GFB.

The transmitter unit can, for example, be made from three lasers with the primary colors red LR, green LG and blue LB. Before the beams are united on an axis with dichroitic mirrors DS, the individual beams are modulated either externally with image modulators MR, MG and MB, or simply directly by means of the excitation current for laser emission. The size and position of the laser scanning point on the retina is adjusted with an actively controllable diaphragm LAA, which is set in the intermediate focus of two lenses in the beam path. Suitable receivers for the scan of the retina reflex image are, for example, photomultipliers, which automatically switch over alternately into a photon-counting mode when the optical signals are very weak and a current-measuring mode when the signals are strong. The use of avalanche photodiodes as receivers is also possible.

The light sources provided for projecting the images back into the eye are semiconductor lasers or miniaturised solid-state lasers with a low continuous-wave power (<300 $\mu$W), which cannot cause any damage to the eye. If semiconductor lasers were used, image modulation could be performed directly, using the lasers' power supply. So that all colors are generated, it is advisable to use three lasers with the primary colors red, green and blue. As the known color triangle of the human sense of sight shows, all the other colors and also the non-colours grey and white can be formed by the color summation of the monochromatic laser lines of those colors. The invention also comprises the possibility of using individual colors as a monochrome solution.

As is illustrated in FIG. 14, the system includes a signal processor SP, which processes the direct image from the retina electronically and synchronously co-ordinates all the functions of the device and of the scanners VSS/HSS, the auxiliary mirror HS, the laser spot adjustment LAA and the size of the field diaphragm GFB. The image processing computer BVC then takes over the image perceived by the eye or images from other technical sensors which are delivered to the computer via an external connection EA, and processes them using predetermined software SW, before they are modulated onto the laser beams as an image signal by means of the signal processor. FIG. 14 illustrates the flow of the optical, electrical and software signals separately. The complete laser unit is indicated by DE, ME refers to the modulation unit, PME to the complete receiver unit, and SUS to the beam switch between the transmitter and receiver unit.

Apart from processing the image currently being processed by the computer, projecting it into the eye and merging it with the original image, laser projection also makes it possible synchronously to superimpose onto the image of the outside world in the eye foreign images which are delivered to the computer externally. If the time between the image capture and its projection is sufficiently short compared to the rapid eye movements, the eye, as when watching a television screen, will no longer perceive any interruption in the image.

The separate but simultaneous image scan on both eyes also detects the differences in perspective of the two images. Since the latter are preserved in both eyes when projected back by the laser, it is ensured that spatial vision is restored.

The components used in the invention are nowadays largely miniaturised and can be obtained inexpensively. For scanning the circular shapes miniaturised tilting mirrors can be used. A second means of producing the circular shapes is to use camera wedge scanners designed for a beam path in transmission. The beam passing through is refracted by a fixed angle by each of the wedges; the total deflection angle can then be continuously adjusted to zero by a fixed rotation of the camera wedges. When the camera wedges are rotated together at a fixed rotation frequency, the deflected beam then describes a circular track. A third possibility is to use an acousto-optical deflection unit, which has the advantage of low inertia and rapid deflection. The variably adjustable auxiliary mirror HS will preferably be a mirror with micro-actuators which is adjustable in two axes.

Suitable means of adjusting the size of the laser spot and the receiving field of vision are preferably micromechanical actuators, such as the kind found in laser printers and CD-players, which are in widespread use.

The beam deflection unit and scanner can be housed in a simple spectacle frame. By means of a glass fiber line, the laser projection unit can be stored in a small housing, for example the size of a paperback, with a battery power supply. Data can be exchanged with a permanently installed external image processing computer either via radio waves or by infrared rays. All the elements of the device of the invention could thus be procured by anyone with no difficulty according to the current state of the art, and the wireless exchange of image data with the external computer would permit that person's unrestricted freedom of movement.

Additional embodiments and suitable elements of the provided systems are described in PCT Application PCT/DE98/01840, filed on Jul. 3, 1998 (published as WO 99/03013) and in PCT Application PCT/DE99/00421, filed on Feb. 16, 1999 (published as WO 99/42315), both of which are incorporated by reference as if fully reproduced herein.

Having described various embodiments and implementations of the present invention, it should be apparent to those skilled in the relevant art that the foregoing is illustrative only and not limiting, having been presented by way of example only. There are other embodiments or elements suitable for the above-described embodiments, described in the above-listed publications, all of which are incorporated by reference as if fully reproduced herein. The functions of any one element may be carried out in various ways in alternative embodiments. Also, the functions of several elements may, in alternative embodiments, be carried out by fewer, or a single, element.

What is claimed is:

1. A system for eye examination by scanning light back-scattered from the retina and for delivering optical signals into the eye, comprising:
    a scanner constructed and arranged to scan an area on the retina;
    a receiver unit, optically coupled to said scanner, constructed and arranged to capture light scattered back from said area of the retina; and
    a projection unit constructed to generate and provide a modulated light configuration to said scanner for delivering said light configuration into the eye relative to said area of the retina; said scanner, said receiver unit and said projection unit being cooperatively designed to analyse a patient's sight wherein said scanner, said receiver unit and said projection unit are designed to further analyse a movement of a patient's eye by generating random dot patterns on the retina of said eye.

2. A system for eye examination by scanning light back-scattered from the retina and for delivering optical signals into the eye, comprising:
    a scanner constructed and arranged to scan an area on the retina;
    a receiver unit, optically coupled to said scanner, constructed and arranged to capture light scattered back from said area of the retina; and
    a projection unit constructed to generate and provide a modulated light configuration to said scanner for delivering said light configuration into the eye relative to said area of the retina, said scanner, said receiver unit and said projection unit being cooperatively designed to determine anomalies in the motor response of the eyeball.

3. The system of claim 2 wherein said scanner, said receiver unit and said projection unit are cooperatively designed to determine anomalies in the motor response of the eyeball by monitoring orientation of the eyeball.

4. The system of claim 2 wherein said scanner, said receiver unit and said projection unit are cooperatively designed to determine the squint angle by determining and monitoring the centre point of both eyes.

5. The system of claim 2 wherein said scanner, said receiver unit and said projection unit are cooperatively designed to detect parasympathetic/sympathetic efferences, by monitoring and evaluating the motor response of the pupil.

6. The system of claim 2 wherein said scanner, said receiver unit and said projection unit are cooperatively designed as a synoptophor.

7. The system of claim 2 wherein said scanner, said receiver unit and said projection unit are cooperatively designed as a synoptometer with no device convergence.

8. The system of claim 2 wherein said scanner, said receiver unit and said projection unit are cooperatively designed as a device for determining cyclodeviation.

9. The system of claim 2 wherein said scanner, said receiver unit and said projection unit are cooperatively designed as a phase difference haploscope.

10. The system of claim 2 wherein said scanner, said receiver unit and said projection unit are cooperatively designed as a device for detecting phoria identical to the visual axis with different lines of sight.

11. A method of eye examination, comprising the acts of:
    scanning an area on the retina;
    capturing light scattered back from said area of the retina;
    generating and scanning a modulated light configuration for delivering said light configuration into the eye relative to said area of the retina; and
    determining anomalies in the motor response of the eyeball based on the captured back-scattered light.

12. The method of claim 11 wherein said determining anomalies in the motor response of the eyeball is performed by monitoring orientation of the eyeball.

* * * * *